US008160710B2

(12) United States Patent
Buysman et al.

(10) Patent No.: US 8,160,710 B2
(45) Date of Patent: Apr. 17, 2012

(54) SYSTEMS AND METHODS FOR IMPLANTING TISSUE STIMULATION ELECTRODES IN THE PELVIC REGION

(75) Inventors: John Jason Buysman, Minnetonka, MN (US); Robert E. Lund, St. Michael, MN (US); James R. Mujwid, Crystal, MN (US); James A. Gohman, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 1224 days.

(21) Appl. No.: 11/775,638

(22) Filed: Jul. 10, 2007

(65) Prior Publication Data

US 2008/0009914 A1    Jan. 10, 2008

Related U.S. Application Data

(60) Provisional application No. 60/806,799, filed on Jul. 10, 2006.

(51) Int. Cl.
*A61N 1/00* (2006.01)
(52) U.S. Cl. ........................................................ 607/41
(58) Field of Classification Search .................... 607/41, 607/129; 600/30
See application file for complete search history.

(56) References Cited

U.S. PATENT DOCUMENTS

| 3,628,538 A | 12/1971 | Vincent et al. |
| 3,640,284 A | 2/1972 | De Langis |
| 3,646,940 A | 3/1972 | Timm et al. |
| 3,650,276 A | 3/1972 | Burghele et al. |
| 3,662,758 A | 5/1972 | Glover |
| 3,667,477 A | 6/1972 | Susset et al. |
| 3,866,613 A | 2/1975 | Kenny et al. |
| 3,870,051 A | 3/1975 | Brindley |
| 3,926,178 A | 12/1975 | Feldzamen |
| 3,941,136 A | 3/1976 | Bucalo |
| 3,983,865 A | 10/1976 | Shepard |
| 3,983,881 A | 10/1976 | Wickham |
| 4,010,758 A | 3/1977 | Rockland et al. |
| 4,023,574 A | 5/1977 | Nemec |
| 4,030,509 A | 6/1977 | Heilman et al. |

(Continued)

FOREIGN PATENT DOCUMENTS

DE    8506522.6 U1    4/1985

(Continued)

OTHER PUBLICATIONS

Dietz et al., Mechanical Properties of Urogynecologic Implant Materials, Int. Urogynecol. J. (2003) 14:239-243.

(Continued)

*Primary Examiner* — Eric D Bertram
*Assistant Examiner* — Roland Dinga
(74) *Attorney, Agent, or Firm* — Kimberly K. Baxter; Gregory L. Koeller

(57) ABSTRACT

Implantable medical devices to relieve problems associated with incontinence and related pelvic disorders and methods of implanting same are disclosed. Stimulation leads for placement in the pelvic floor have fixation mechanisms for stabilization of the stimulation electrodes to inhibit dislodgement from a selected stimulation site. In certain embodiments, the fixation mechanisms encourage fibrosis about the lead to chronically stabilize the position of the stimulation lead and/or stimulation electrode(s). In certain embodiments, the fixation mechanisms are isolated from body tissue during routing of the stimulation lead through a tissue pathway and then exposed to body tissue to encourage fibrosis.

8 Claims, 20 Drawing Sheets

U.S. PATENT DOCUMENTS

| | | |
|---|---|---|
| 4,044,774 A | 8/1977 | Corbin et al. |
| 4,106,511 A | 8/1978 | Erlandsson |
| 4,136,684 A | 1/1979 | Scattergood et al. |
| 4,139,006 A | 2/1979 | Corey |
| 4,153,059 A | 5/1979 | Fravel et al. |
| 4,157,087 A | 6/1979 | Miller et al. |
| 4,165,750 A | 8/1979 | Aleev et al. |
| 4,177,819 A | 12/1979 | Kofsky et al. |
| 4,222,377 A | 9/1980 | Burton |
| 4,290,420 A | 9/1981 | Manetta |
| 4,387,719 A | 6/1983 | Plevnik et al. |
| 4,402,328 A | 9/1983 | Doring |
| 4,406,288 A | 9/1983 | Horwinski et al. |
| 4,414,986 A | 11/1983 | Dickhudt et al. |
| 4,431,001 A | 2/1984 | Hakansson et al. |
| 4,457,299 A | 7/1984 | Cornwell |
| 4,492,233 A | 1/1985 | Petrofsky et al. |
| 4,515,167 A | 5/1985 | Hochman |
| 4,542,753 A | 9/1985 | Brenman et al. |
| 4,568,339 A | 2/1986 | Steer |
| 4,569,351 A | 2/1986 | Tang |
| 4,571,749 A | 2/1986 | Fischell |
| 4,580,578 A | 4/1986 | Barsom |
| 4,585,005 A | 4/1986 | Lue et al. |
| 4,602,624 A | 7/1986 | Naples et al. |
| 4,607,639 A | 8/1986 | Tanagho et al. |
| 4,628,942 A | 12/1986 | Sweeney et al. |
| 4,688,575 A | 8/1987 | DuVall |
| 4,703,755 A | 11/1987 | Tanagho et al. |
| 4,731,083 A | 3/1988 | Fischell |
| 4,739,764 A | 4/1988 | Lue et al. |
| 4,750,494 A | 6/1988 | King |
| 4,771,779 A | 9/1988 | Tanagho et al. |
| 4,785,828 A | 11/1988 | Maurer |
| 4,881,526 A | 11/1989 | Johnson et al. |
| 4,913,164 A | 4/1990 | Greene et al. |
| 4,941,874 A | 7/1990 | Sandow et al. ............... 604/60 |
| 5,013,292 A | 5/1991 | Lemay |
| 5,019,032 A | 5/1991 | Robertson |
| 5,082,006 A | 1/1992 | Jonasson |
| 5,094,242 A | 3/1992 | Gleason et al. |
| 5,103,835 A | 4/1992 | Yamada et al. |
| 5,112,344 A | 5/1992 | Petros |
| 5,193,539 A | 3/1993 | Schulman et al. |
| 5,193,540 A | 3/1993 | Schulman et al. |
| 5,199,430 A | 4/1993 | Fang et al. |
| 5,285,781 A | 2/1994 | Brodard |
| 5,291,902 A | 3/1994 | Carman |
| 5,312,439 A | 5/1994 | Loeb |
| 5,324,316 A | 6/1994 | Schulman et al. |
| 5,324,324 A | 6/1994 | Vachon et al. |
| 5,330,507 A | 7/1994 | Schwartz |
| 5,358,514 A | 10/1994 | Schulman et al. |
| 5,405,367 A | 4/1995 | Schulman et al. |
| 5,411,548 A | 5/1995 | Carman |
| 5,417,226 A | 5/1995 | Juma |
| 5,423,329 A | 6/1995 | Ergas |
| 5,452,719 A | 9/1995 | Eisman et al. |
| 5,484,445 A | 1/1996 | Knuth |
| 5,518,504 A | 5/1996 | Polyak |
| 5,520,606 A | 5/1996 | Schoolman et al. |
| 5,562,717 A | 10/1996 | Tippey et al. |
| 5,569,351 A | 10/1996 | Menta et al. |
| 5,571,148 A | 11/1996 | Loeb et al. |
| 5,611,515 A | 3/1997 | Benderev et al. |
| 5,611,768 A | 3/1997 | Tutrone, Jr. |
| 5,634,462 A | 6/1997 | Tyler et al. |
| 5,702,428 A | 12/1997 | Tippey et al. |
| 5,752,978 A | 5/1998 | Chancellor |
| 5,807,397 A | 9/1998 | Barreras |
| 5,824,027 A | 10/1998 | Hoffer et al. |
| 5,833,595 A | 11/1998 | Lin |
| 5,842,478 A | 12/1998 | Benderev et al. |
| 5,860,425 A | 1/1999 | Benderev et al. |
| 5,899,909 A | 5/1999 | Claren et al. |
| 5,927,282 A | 7/1999 | Lenker et al. |
| 5,931,864 A | 8/1999 | Chastain et al. ............... 607/128 |
| 5,954,761 A | 9/1999 | Machek et al. |
| 5,957,920 A | 9/1999 | Baker |
| 5,957,965 A | 9/1999 | Moumane et al. |
| 5,978,712 A | 11/1999 | Suda et al. |
| 5,984,854 A | 11/1999 | Ishikawa et al. |
| 6,002,964 A | 12/1999 | Feler et al. |
| 6,026,326 A | 2/2000 | Bardy |
| 6,027,456 A | 2/2000 | Feler et al. |
| 6,039,686 A | 3/2000 | Kovac |
| 6,042,534 A | 3/2000 | Gellman et al. |
| 6,051,017 A | 4/2000 | Loeb et al. |
| 6,055,456 A | 4/2000 | Gerber |
| 6,061,596 A | 5/2000 | Richmond et al. |
| 6,104,955 A | 8/2000 | Burgeois |
| 6,104,960 A | 8/2000 | Duysens et al. |
| 6,110,101 A | 8/2000 | Tihon et al. |
| 6,131,575 A | 10/2000 | Lenker et al. |
| 6,135,945 A | 10/2000 | Sultan |
| 6,141,594 A * | 10/2000 | Flynn et al. ............... 607/127 |
| 6,161,029 A | 12/2000 | Spreigl et al. ............... 600/381 |
| 6,178,356 B1 | 1/2001 | Chastain et al. ............... 607/128 |
| 6,185,452 B1 | 2/2001 | Schulman et al. |
| 6,208,894 B1 | 3/2001 | Schulman et al. |
| 6,240,315 B1 | 5/2001 | Mo et al. |
| 6,240,316 B1 | 5/2001 | Richmond et al. |
| 6,243,607 B1 | 6/2001 | Mintchev et al. |
| 6,266,557 B1 | 7/2001 | Roe et al. |
| 6,266,564 B1 | 7/2001 | Hill et al. |
| 6,304,786 B1 * | 10/2001 | Heil et al. ............... 607/126 |
| 6,328,686 B1 | 12/2001 | Kovac |
| 6,341,236 B1 | 1/2002 | Osorio et al. |
| 6,354,991 B1 | 3/2002 | Gross et al. |
| 6,360,750 B1 | 3/2002 | Gerber et al. |
| 6,366,814 B1 | 4/2002 | Boveja et al. |
| 6,382,214 B1 | 5/2002 | Raz et al. |
| 6,397,109 B1 | 5/2002 | Cammilli et al. ............... 607/123 |
| 6,407,308 B1 | 6/2002 | Roe et al. |
| 6,418,930 B1 | 7/2002 | Fowler |
| 6,505,082 B1 * | 1/2003 | Scheiner et al. ............... 607/123 |
| 6,582,441 B1 | 6/2003 | He et al. ............... 606/129 |
| 6,600,956 B2 | 7/2003 | Maschino et al. |
| 6,612,977 B2 | 9/2003 | Staskin et al. |
| 6,641,524 B2 | 11/2003 | Kovac |
| 6,650,943 B1 | 11/2003 | Whitehurst et al. |
| 6,652,449 B1 | 11/2003 | Gross et al. |
| 6,652,450 B2 | 11/2003 | Neisz et al. |
| 6,652,499 B1 | 11/2003 | Edgren et al. |
| 6,658,297 B2 | 12/2003 | Loeb |
| 6,659,936 B1 | 12/2003 | Furness et al. |
| 6,712,772 B2 | 3/2004 | Cohen et al. |
| 6,735,474 B1 | 5/2004 | Loeb et al. |
| 6,802,807 B2 | 10/2004 | Anderson et al. |
| 6,862,480 B2 | 3/2005 | Cohen et al. |
| 6,896,651 B2 | 5/2005 | Gross et al. |
| 6,911,003 B2 | 6/2005 | Anderson et al. |
| 6,941,171 B2 | 9/2005 | Mann et al. |
| 6,952,613 B2 | 10/2005 | Swoyer et al. |
| 6,964,643 B2 | 11/2005 | Hovland et al. |
| 6,964,699 B1 | 11/2005 | Carns et al. |
| 6,971,393 B1 | 12/2005 | Mamo et al. |
| 7,079,882 B1 | 7/2006 | Schmidt |
| 7,120,499 B2 | 10/2006 | Thrope et al. |
| 7,319,905 B1 * | 1/2008 | Morgan et al. ............... 607/129 |
| 7,328,068 B2 | 2/2008 | Spinelli et al. |
| 7,330,764 B2 | 2/2008 | Swoyer et al. |
| 7,343,202 B2 | 3/2008 | Mrva et al. |
| 7,376,467 B2 | 5/2008 | Thrope et al. |
| 7,613,516 B2 | 11/2009 | Cohen et al. |
| 7,628,795 B2 | 12/2009 | Karwoski et al. |
| 7,647,113 B2 | 1/2010 | Wirbisky et al. |
| 7,771,345 B1 | 8/2010 | O'Donnell ............... 600/29 |
| 2001/0002441 A1 | 5/2001 | Boveja |
| 2001/0003799 A1 | 6/2001 | Boveja |
| 2001/0018549 A1 | 8/2001 | Scetbon |
| 2002/0055761 A1 | 5/2002 | Mann et al. |
| 2002/0099259 A1 * | 7/2002 | Anderson et al. ............... 600/29 |
| 2002/0161382 A1 | 10/2002 | Neisz et al. |
| 2002/0165566 A1 | 11/2002 | Ulmsten |
| 2003/0018365 A1 | 1/2003 | Loeb |
| 2003/0023296 A1 | 1/2003 | Osypka ............... 607/122 |

| | | | |
|---|---|---|---|
| 2003/0028232 A1 | 2/2003 | Camps et al. | |
| 2003/0060868 A1* | 3/2003 | Janke et al. | 607/123 |
| 2003/0100930 A1 | 5/2003 | Cohen et al. | |
| 2003/0171644 A1 | 9/2003 | Anderson et al. | |
| 2003/0199961 A1 | 10/2003 | Bjorklund et al. | 607/126 |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0039453 A1 | 2/2004 | Anderson et al. | |
| 2004/0059392 A1 | 3/2004 | Parramon et al. | |
| 2004/0068203 A1 | 4/2004 | Gellman et al. | |
| 2004/0093053 A1 | 5/2004 | Gerber et al. | |
| 2004/0242956 A1 | 12/2004 | Scorvo | |
| 2004/0248979 A1 | 12/2004 | Brettman et al. | |
| 2005/0038489 A1 | 2/2005 | Grill | |
| 2005/0043580 A1 | 2/2005 | Watschke et al. | |
| 2005/0065395 A1 | 3/2005 | Mellier | |
| 2005/0113877 A1 | 5/2005 | Spinelli et al. | |
| 2005/0119710 A1 | 6/2005 | Furness et al. | |
| 2005/0143618 A1 | 6/2005 | Anderson et al. | |
| 2005/0149156 A1 | 7/2005 | Libbus et al. | 607/119 |
| 2005/0216069 A1 | 9/2005 | Cohen et al. | |
| 2005/0228346 A1 | 10/2005 | Goode et al. | 604/164.07 |
| 2005/0245787 A1 | 11/2005 | Cox et al. | |
| 2005/0245874 A1 | 11/2005 | Carrez et al. | |
| 2005/0250977 A1 | 11/2005 | Montpetit et al. | |
| 2005/0283235 A1 | 12/2005 | Kugler et al. | |
| 2006/0004421 A1 | 1/2006 | Bennett et al. | |
| 2006/0004429 A1 | 1/2006 | Mrva et al. | |
| 2006/0149345 A1 | 7/2006 | Bogg, II et al. | |
| 2006/0241733 A1 | 10/2006 | Zhang et al. | 607/122 |
| 2006/0287571 A1 | 12/2006 | Gozzi et al. | |
| 2007/0021650 A1 | 1/2007 | Rocheleau et al. | |
| 2007/0043416 A1 | 2/2007 | Callas et al. | |
| 2007/0123952 A1 | 5/2007 | Strother et al. | |
| 2007/0179559 A1 | 8/2007 | Giftakis et al. | |
| 2007/0185541 A1 | 8/2007 | DiUbaldi et al. | |
| 2007/0239224 A1 | 10/2007 | Bennett et al. | |
| 2007/0253997 A1 | 11/2007 | Giftakis et al. | |
| 2007/0253998 A1 | 11/2007 | Giftakis et al. | |
| 2007/0255333 A1 | 11/2007 | Giftakis et al. | |
| 2007/0255341 A1 | 11/2007 | Giftakis et al. | |
| 2007/0260288 A1 | 11/2007 | Gross | |
| 2007/0265675 A1 | 11/2007 | Lund et al. | |
| 2008/0071321 A1 | 3/2008 | Boggs, II et al. | |
| 2008/0132969 A1 | 6/2008 | Bennett et al. | |
| 2009/0012592 A1 | 1/2009 | Buysman et al. | |
| 2009/0043356 A1 | 2/2009 | Longhini et al. | |
| 2009/0157091 A1 | 6/2009 | Buysman | |
| 2010/0049289 A1 | 2/2010 | Lund et al. | |
| 2010/0076254 A1 | 3/2010 | Jimenez et al. | |

FOREIGN PATENT DOCUMENTS

| | | |
|---|---|---|
| EP | 0245547 | 5/1986 |
| EP | 1 661 600 A1 | 5/2006 |
| EP | 1119314 B1 | 6/2006 |
| GB | 2309388 | 7/1997 |
| WO | 9012617 | 11/1990 |
| WO | 9604955 | 2/1996 |
| WO | 9632916 | 10/1996 |
| WO | 9817190 A2 | 4/1998 |
| WO | 0000082 A1 | 1/2000 |
| WO | 0019940 A1 | 4/2000 |
| WO | 0239890 A2 | 5/2002 |
| WO | 02069781 A2 | 9/2002 |
| WO | 02078592 | 10/2002 |
| WO | 03002192 | 1/2003 |
| WO | 2006047833 | 5/2006 |
| WO | 2007097994 A2 | 8/2007 |
| WO | 2007126632 A3 | 11/2007 |
| WO | 2007145913 A1 | 12/2007 |
| WO | 2010107751 A2 | 9/2010 |

OTHER PUBLICATIONS

Iglesia et al., "The Use of Mesh in Gynecologic Surgery", Int. Urogynecol J. (1997) 8:105-115.

Partial European Search Report from European Patent Application No. 10176162.5, mailed Jan. 21, 2011.

Yamamoto et al., "Optimal parameters for effective electrical stimulation of the anal sphincters in a child with fecal incontinence: preliminary report," Pediatr Surg Int (1993) 8:132-137.

Yamanishi et al., "Electrical Stimulation for Stress Incontinence", Int. Urogynecol J (1998) 9:281-290 Springer-Verlag London Ltd.

Office Action from related U.S. Appl. No. 12/170,582, mailed Nov. 24, 2010.

Notification of a First Office Action from Chinese patent application 200780007709.2, mailed Sep. 27, 2010.

European Search Report and Written Opinion of 06011641.5, dated Aug. 21, 2006.

International Search Report and Written Opinion of PCT/US2007/004474, filed Feb. 22, 2007.

International Search Report and Written Opinion of PCT/US2007/000112, filed Jan. 3, 2007.

U.S. Appl. No. 61/160,765, filed Mar. 17, 2009.

U.S. Appl. No. 12/406,434, filed Mar. 18, 2009.

Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.

Caldwell, K.P.S. "Electrical Stimulation.", Sphincter Research Unit, Royal Devon and Exeter Hospital, Exeter (England), Urol. Int. 29: 225, 1974 (1 page).

Caldwell, K.P.S. "The Use of Electrical Stimulation in Urinary Retention and Incontinence [Abridged]." Section of Urology, vol. 61, pp. 35-39, Jul. 1968.

Caldwell, K.P.S. et al. "Urethral Pressure Recordings in Male Incontinents Under Electrical Stimulation." Investigative Urology vol. 5, No. 6, pp. 572-579, May 1968.

Notification of Transmittal of the International Search Report and Written Opinion for International Application No. PCT/US2011/023677 dated Apr. 21, 2011.

European Search Report and European Search Opinion for European patent application No. 10176162.5 dated Apr. 28, 2011.

Office Action from U.S. Appl. No. 12/170,582 dated Apr. 12, 2011.

Office Action from U.S. Appl. No. 12/170,582, dated Aug. 2, 2011.

* cited by examiner

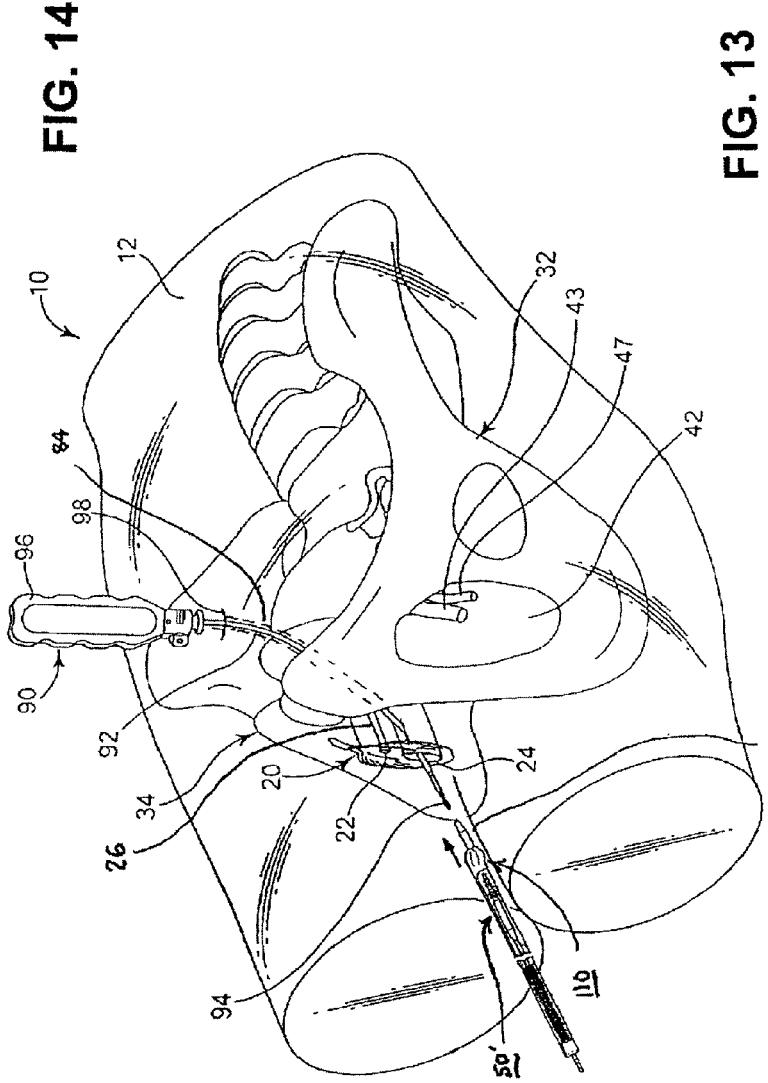
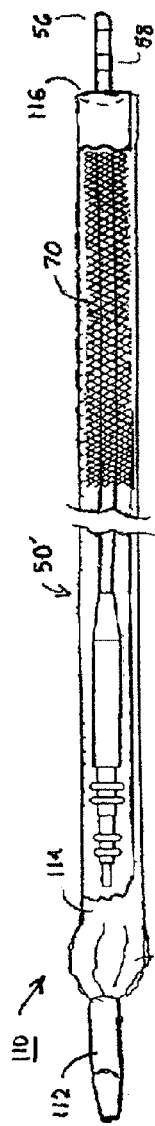

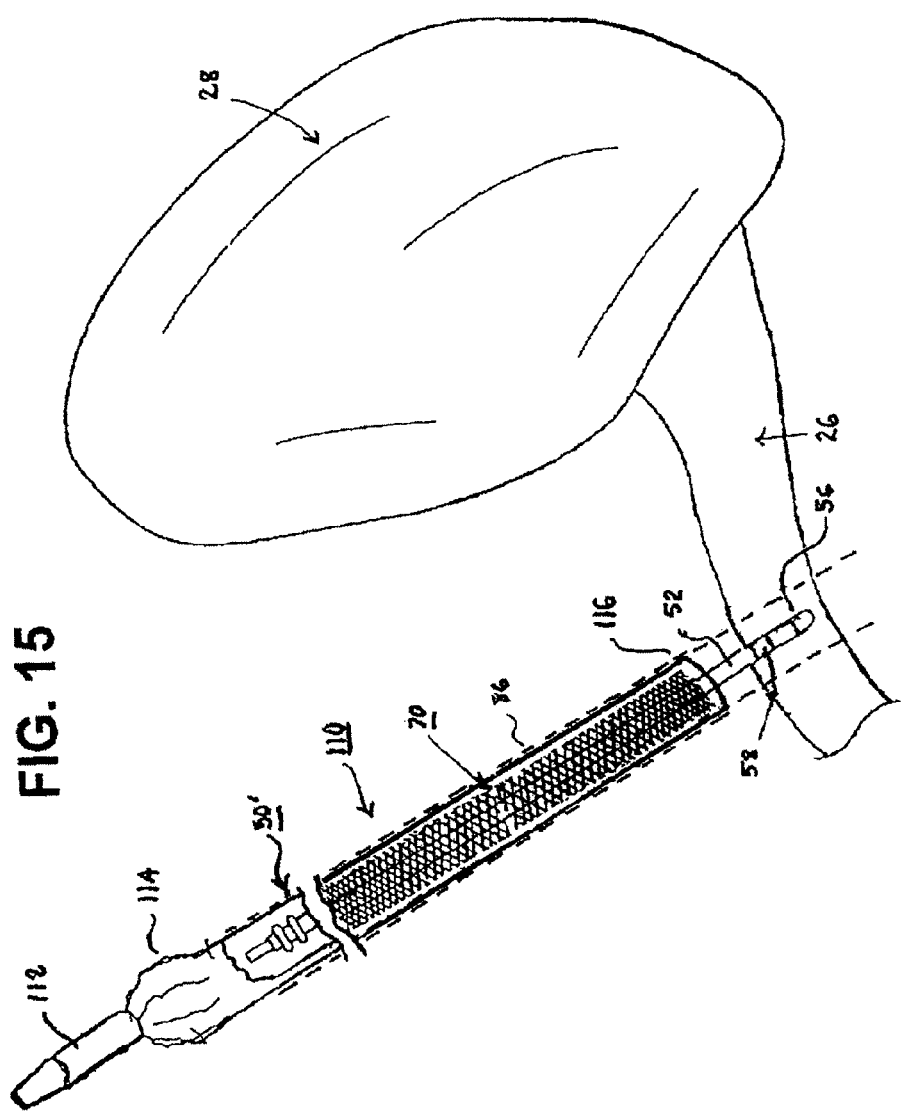

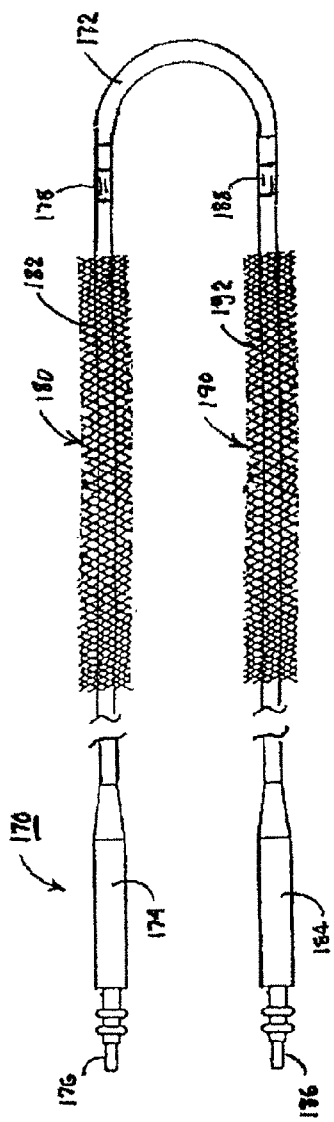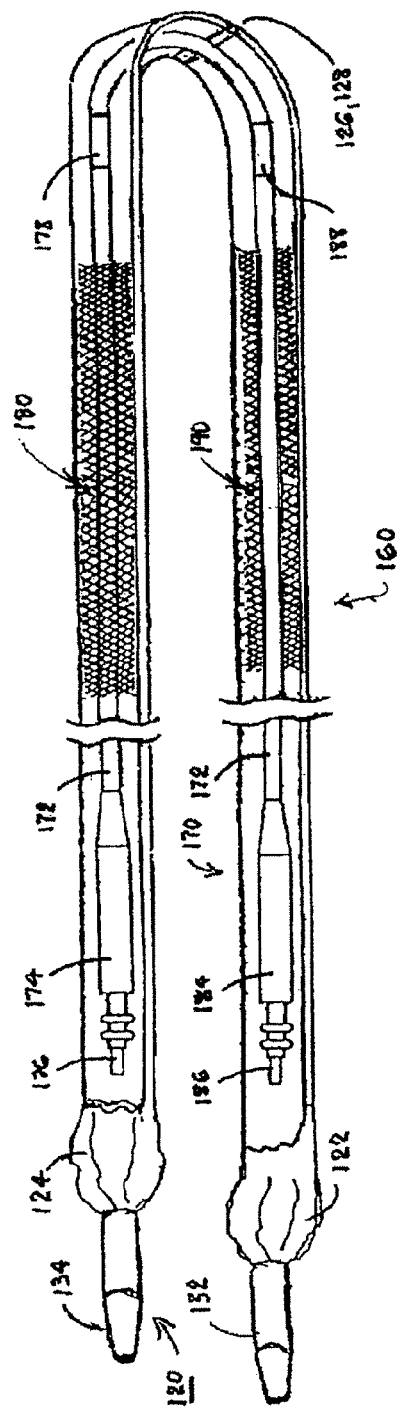
FIG. 19
FIG. 20

SYSTEMS AND METHODS FOR IMPLANTING TISSUE STIMULATION ELECTRODES IN THE PELVIC REGION

CROSS-REFERENCE TO RELATED APPLICATIONS

This application claims priority under 35 USC §119(e) to U.S. Provisional Application Ser. No. 60/806,799 filed Jul. 10, 2006, the entire contents of which is incorporated herein by reference.

Reference is hereby made to commonly assigned, copending U.S. patent application Ser. No. 11/418,790, filed May 5, 2006, entitled "Apparatus for Treating Stress & Urge Incontinence" and incorporated herein by reference.

Reference is hereby made to commonly assigned, copending PCT Application No. PCT/US2007/004474 filed Feb. 22, 2007, entitled "Electrode Sling for Treating Stress and Urge Incontinence" and incorporated herein by reference.

TECHNICAL FIELD

The present invention relates generally to implantable medical devices, and specifically to implantable medical devices to relieve problems associated with incontinence and related pelvic disorders.

BACKGROUND

Implantable medical devices (IMDs) that generate and apply to excitable muscle tissue, nerves, and organs in the pelvic region to treat pelvic floor disorders are clinically available or have been proposed. Pelvic floor disorders include urinary and fecal incontinence, erectile dysfunction, and pelvic pain.

As set forth in U.S. Pat. No. 6,964,699, urinary incontinence is a significant clinical problem and a major source of disability and dependency. The most frequently occurring types of urinary incontinence are stress incontinence, urge incontinence, overflow incontinence, and mixed incontinence characterized by involuntary loss of urine, beyond the individual's control, due to the loss or diminution of the ability to maintain the urethral sphincter closed as the bladder fills with urine. Muscles involved in controlling the urinary flow include primarily the urethral sphincter and the levator ani, with the cooperation of fibromuscular extensions along the urethra and other muscles in the general region of the pelvic diaphragm.

Fecal incontinence is a condition characterized by involuntary defecation or passage of feces through the anal canal due to injury to or weakness of one or more of the internal anal sphincter, the external anal sphincter, and the levator ani.

As set forth in U.S. Pat. No. 6,896,651, male or female stress urinary incontinence (SUI) occurs and results from weakness or inability of pelvic muscles to hold back urinary flow from the bladder when abdominal pressure increases due to common physical or emotional stress events, such as coughing, laughing or mild physical exertion. Stress incontinence is typically associated with either or both of urethral hypermobility and intrinsic sphincter deficiency. Urethral hypermobility is characterized by weakness of or injury to pelvic floor muscles that causes the bladder to descend during abdominal straining or pressure, allowing urine to leak out of the bladder. Intrinsic sphincter deficiency is characterized by the inability of the urethral musculature to completely close the urethra or keep it closed during stress.

In urge incontinence, a sudden, urgent need to pass urine causes involuntary urination, before the patient can get to a toilet. The condition may be caused by damage to nerve pathways from the brain to the bladder or by psychosomatic factors, leading to involuntary bladder contraction. Overflow incontinence occurs when the bladder is unable to empty normally. Weak bladder muscles, caused e.g. by nerve damage from diabetes, or a blocked urethra, caused e.g. by tumors or urinary stones, are among the more common causes of overflow incontinence. Frequency or urgency involves the need or urge to urinate on an excessively frequent or habitual basis. Some patients exhibit combinations of these types of incontinence that are often called mixed incontinence.

Many options are available to treat incontinence in its various forms, including Kegel exercises, biofeedback, timed voiding or bladder training, medications, pessaries, invasive or minimally invasive surgery, catheterization, and implantation IMDs. Urinary incontinence IMDs are typically implanted in relation to the tissue structure around the urethra including the urethral wall, the bladder neck, bladder suspension ligaments, the urethral sphincter, pelvic ligaments, pelvic floor muscles, fascia, and the like. Urinary incontinence IMDs include urethral tapes or slings that support the urethra, prosthetic sphincter systems that compress the urethra until voiding is initiated, and periurethral or transurethral injection of a mass of biocompatible bulk-enhancing or bulking agent or an inflatable balloon into the tissue structure around the urethra.

Male and female urethral sling procedures are disclosed in commonly assigned U.S. Pat. Nos. 6,382,214 and 6,652,450, for example, and further female urethral sling procedures are described in commonly assigned U.S. Pat. Nos. 6,641,524 and 6,612,977, and in U.S. Patent Application Publication Nos. 2002/0165566 and 2005/0245787, for example, and publications and patents cited therein. The implantation of certain urethral slings involves the use of delivery systems configured for and techniques that involve transvaginal, transobturator, supra-pubic and pre-pubic exposures or pathways.

In surgical approaches disclosed, for example, in commonly assigned U.S. Patent Application Publication Nos. 2005/0043580 and 2005/0065395, elongated self-fixating urethral slings are implanted for treating female prolapse employing a pair of sling implantation instruments or tools. The sling implantation tools comprise a handle with an elongated needle portion terminating in a needle distal end adapted to be coupled to free ends of the urethral sling and have mirror image right and left handed needle shapes.

The sling implantation tools disclosed in the above-referenced 2005/0043580 publication have a curvature in a single plane and correspond generally to the BioArc™ SP and SPARC™ single use sling implantation tools sold by American Medical Systems, Inc., (Minnetonka, Minn.) in a kit with an elongated urethral sling. The sling implantation tools disclosed in the above-referenced 2005/00653985 publication have a curvature in 3-dimensional space and correspond generally to the BioArc™ TO and MONARC™ TO single use sling implantation tools sold by American Medical Systems, Inc., in a kit with an elongated urethral sling. In each such sling implantation tool, the needle portion has a proximal straight portion extending from the handle and a distal shaped portion terminating in a needle distal end. The needle portion is sized and shaped so that the distal end may initially be moved through an abdominal incision and advanced posterior to one of the right and left posterior ischiopubic pubic ramus of the pelvic girdle spaced from the bladder to a urethral incision accessing the urethral tissue structure, e.g., a vaginal incision in the region of the vaginal apex of a female patient.

The needles of the BioArc™ TO and MONARC™ TO implantation tools are curved in three-dimensional space so that the needle tip may be advanced toward and through the obturator membrane of the obturator foramen, and then toward a vaginal incision in the region of the vaginal apex. The surgeon employs a learned wrist motion of the hand grasping the handle and pressure feedback felt through the handle to guide advancement. Also, the surgeon may palpate the vaginal wall with the fingers of the free hand to locate the needle tip and guide it toward and through the vaginal incision to expose the needle tip. The procedure is repeated using the other of the right and left hand sling implantation tools to advance the needle tip through a second skin incision and the other of the respective right and left obturator membranes to expose both needle tips through vaginal incisions.

In the above-referenced U.S. Patent Application Publication No. 2002/0165566, a curved needle is provided having a detachable handle for making a similar tissue pathway by extending the needle end through the vaginal incision, through the tissue, and then out an abdominal skin incision. The handle is detached, and the sling end coupled to the needle end extending from the vaginal incision. The needle end extending from the abdominal skin incision is then grasped to pull the sling through the tissue pathway so that the sling end can be detached from the needle end outside the abdominal incision.

Returning to the use of the BioArc™ TO and MONARC™ TO implantation tools, right and left subcutaneous transobturator pathways are formed through the right and left obturator foramen and connective tissue attached to the right and left posterior ischiopubic pubic ramus of the pelvic girdle. This procedure is preformed without visualization of the needle tip, and care must be taken to avoid deviating posteriorly and penetrating the bladder and to otherwise avoid damaging any of the obturator nerves, the superficial epigastric vessel, the inferior epigastric vessel, the external iliac artery and the internal iliac artery.

The free ends of the elongated urethral slings are implanted through the tissue pathways employing the right handed and left handed sling implantation tools as further described in the above-referenced U.S. Patent Application Publication Nos. 2005/0043580 and 2005/0065395. Generally speaking, the free ends of the elongated urethral slings are coupled to the needle distal ends, and portions of the sling are drawn through the pathways to draw a central sling portion against the urethra to provide support. The free ends of the elongated urethral slings include dilating connectors for connecting with the needle distal ends so that the pathways are dilated as the connectors are drawn through them. The dilating connectors are drawn out through the abdominal skin incisions and are severed from the urethral sling. The urethral sling portions other than the central portion may be covered with a detachable protective film sheath that is then withdrawn exposing mesh that is sutured to subcutaneous tissue layers. Chronic tissue ingrowth into the mesh pores stabilizes the urethral sling. A similar procedure creating a tissue pathway from a urethral incision accessing the urethral tissue structure and an abdominal skin incision may be followed to install an elongated urethral sling to support the male urethra to alleviate incontinence as described in regard to certain embodiments in the above-referenced '450 patent.

In another approach, a neuromodulator or neurostimulator implantable medical device (IMD) is implanted in a patient's body to electrically stimulate nerves controlling external sphincter and bladder functions, e.g., the sacral nerves in the nerve root or at the peripheral sciatic nerve or the pudendal nerve. In still another approach a muscle tissue stimulator IMD is implanted in a patient's body to directly electrically excitable muscle tissue of a sphincter, e.g., tissue structure around the urethra or anus. The IMD in either case comprises a medical electrical lead, also known as a neural lead or tissue stimulation lead, and an implantable pulse generator (IPG).

According to several known surgical treatment methods for implanting a neurostimulator IMD to stimulate a nerve, one or more nerve stimulation or neural stimulation electrode supported at the distal end of a neural lead is disposed at a nerve stimulation site. It is typically necessary to employ introducers and stiffening stylets and/or guidewires to position the distal neural stimulation electrode(s) in operative relation to a nerve at the target stimulation site. A proximal lead connector assembly is coupled to a connector header of the IPG, so that the IPG and neural lead comprise the neurostimulator IMD. See for example, U.S. Pat. Nos. 5,569,351, 4,607,639, 4,739,764, 4,771,779, and 6,055,456 regarding electrical stimulation of the sacral nerve to control bladder function. The InterStim® System for Urinary Control sold by Medtronic, Inc., Fridley, Minn., comprises such an IPG, which is surgically implanted in the lower abdomen, and a medical electrical lead that extends from a connection with the IPG to exposed neural stimulation electrodes disposed adjacent the sacral nerve near the sacrum (the bone at the base of the spine) in a major surgical procedure—sometimes six hours under general anesthesia. The IPG continuously generates electrical stimulation pulses that are applied to the sacral nerve to control urinary voiding. The continuous electrical stimulation of the nerve has been found to control urge incontinence in some patients.

Stimulation of the pudendal nerve employing a neurostimulator IMD as an alternative to sacral nerve stimulation has long been proposed. Electrical stimulation delivered by an intravaginal or a perineal surface electrode has been shown to inhibit premature and inappropriate detrusor contractions. The mechanism for such effects appears to derive from the electrical stimulation of pudendal nerve afferents (sensory receptors or sensory nerve fibers). Input into the pudendal afferent system inhibits a parasympathetic reflex loop consisting of bladder wall afferents (sensory reflexes) and efferents (motor reflexes). This parasympathetic loop normally senses a distension of the bladder via the afferent limb and responds by sending an efferent signal to contract the bladder. Although such stimulation has shown therapeutic effects, electrode placement and on-going stimulation do not lend themselves easily to chronic stimulation.

Stimulation of the tissue structure around the urethra is also proposed in the above-referenced '651 patent, in U.S. Pat. No. 6,862,480, and in Application Publication No. 2005/0216069, all assigned to Biocontrol Medical, Ltd., to treat both urinary stress incontinence and urge incontinence. The tissue stimulator IMD comprises a control unit or IPG coupled through medical electrical leads to one or more sense/stimulation electrodes and to one or more mechanical sensor. The IPG is preferably implanted under the skin of the abdomen or genital region, the sense/stimulation electrodes are preferably implanted in the pelvic region so as to be in electrical contact with one or more of the muscles that regulate urine flow from the bladder, e.g., the urethral sphincter and the levator ani, and the mechanical sensors are preferably implanted on, in or in the vicinity of the bladder. The sense/stimulation electrodes are described as flexible wire, intramuscular-type, electrodes, about 1-5 mm long and 50-100 microns in diameter, and may be formed in the shape of a spiral or hook, so that the shape facilitates fixation in tissue. The mechanical sensors supported on a sensor lead body comprise one or more pressure, force, motion or acceleration sensor, or an ultrasound transducer, that generate signals responsive to motion, to intravesical or abdominal pressure, or to urine volume in the bladder, and are thus indicative of possible imminent incontinence.

The IPG receives and processes electromyographic (EMG) signals sensed across the electrodes and the mechanical sensor output signal to distinguish between EMG signals indicative of urge incontinence, EMG signals indicative of stress incontinence, and EMG signals that are not due to incontinence. Electrical stimulation having stimulation parameters tailored to inhibit urge incontinence are generated by the IPG and delivered across the electrodes when the sensed signals are indicative of impending urge incontinence. Similarly, electrical stimulation having stimulation parameters tailored to inhibit stress incontinence are generated by the IPG and delivered across the electrodes when the sensed signals are indicative of impending stress incontinence. Certain implantation methods for implanting the tissue stimulation IPG in the body of a female patient are described in the '651 and '480 patents. It is suggested that similar methods would be employed in the implantation of the IMD in a male patient.

In one method, a subcutaneous surgical pocket is made to receive the IPG approximately 1 cm cephalad to the pubic bone. A vaginal mucosa incision is made at a site approximately 0.5-1 cm anterior and lateral to the urethral meatus. A subcutaneous pathway is tunneled between the pocket and the vaginal mucosa incision, and the lead body is extended through the pathway to dispose a distal portion of the lead outside the vaginal mucosa incision. A 5 French, splittable short introducer is inserted into the vaginal mucosa incision adjacent to the lead and advanced with care slightly medially, i.e., towards the urethra, about 2.5 cm, to a site 0.5-1 cm lateral to the urethral wall. The distal end of the stimulation lead is inserted and advanced through the lumen of the short introducer into the urethral sphincter. The introducer sleeve is split apart to withdraw it over the lead body after the stimulation electrode is properly positioned. The stimulation lead body is sutured to the subcutaneous tissue to secure it from movement. The exposed distal portion of the lead body is retracted subcutaneously, and the vaginal mucosa incision is closed.

To implant the sensor lead, an 8 French introducer is inserted through the pocket incision, between the fascia and muscle tissue, and advanced into the retropubic space. The sensor lead bearing a distal pressure or electrical sensor is stiffened by a stiffening stylet and the lead body is advanced through the introducer to dispose the sensor at a desired position, e.g., in the retropubic space or between fascia and muscle. The sensor lead body is also sutured to the fascia, the stylet is withdrawn, and the introducer is removed. The sensor lead and stimulation lead connectors are coupled to the IPG. The IPG is disposed in the pocket and the pocket is closed after testing the IMD to ascertain that all connections are secure and that sensing and stimulation can be reliably provided.

This method of positioning the stimulation electrodes in or proximate the urethral sphincter surrounding the urethra can be troublesome since there is a tendency that the stimulation electrode will be retracted when the introducer sleeve is split and withdrawn. In addition, the routing of the lead body through the subcutaneous pathway relative to the pubic bone can also stress the lead body and contribute to electrode dislodgement. Suturing the lead body to elastic tissue does not necessarily inhibit dislodgement. Moreover, care must be taken in placing sutures directly against a lead body to avoid damage to the insulating sheath or the conductors within the sheath. A suture sleeve may be employed, but it may be difficult to locate the relatively bulky sleeve in a place where suturing to tissue would be effective.

A wide variety of active (tissue penetrating) and passive (non-penetrating) fixation mechanisms have been proposed to retain cardiac pacing electrodes, cardioversion/defibrillation electrodes, brain stimulation electrodes, and neural stimulation electrodes at a selected stimulation site. Active fixation helical screws and hooks are not suitable for fixation to or about nerves due to the potential for nerve damage during implantation or due to micro-dislodgement in chronic implantation. A wide variety of passive fixation tines and shaped lead bodies are employed or proposed for sacral nerve and epidural space stimulation electrodes. It is also suggested that hook or spiral active fixation devices be incorporated at the distal ends of tissue stimulation leads disclosed in the above-referenced '651 and '480 patents and in Application Publication No. 2005/0216069. Unlike the myocardium of the heart, the tissue structure adjacent the urethra or anus is relatively soft, and hook or spiral active fixation devices do not hold as well as they do in the myocardium.

It is also suggested in U.S. Pat. No. 4,010,758 disclosing a pacing lead that a Dacron mesh suture pad surrounding an active fixation, helical, spiral-shaped electrode may promote tissue ingrowth chronically to augment the fixation achieved acutely. In use, the spiral-shaped electrode is screwed into the myocardium, and the mesh suture pad is sutured to the myocardium. Stomach wall stimulation leads are disclosed in U.S. Pat. No. 6,952,613 that employ similar helical and hook shaped active fixation mechanisms having such a Dacron mesh suture pad that is adapted to be sutured to the tissue.

It would be desirable to provide alternative fixation mechanisms to stabilize the distal tissue stimulation electrodes of tissue stimulation leads at stimulation sites in the pelvic region to treat selected pelvic disorders.

SUMMARY OF THE INVENTION

One aspect of the invention involves implantation tools, kits, systems, and methods for use in the implantation of tissue stimulation IMDs for delivering tissue stimulation through tissue stimulation electrode(s) to selected sites in the pelvic region to treat selected pelvic disorders. Stimulated tissues and tissue structures may include muscle and/or nerve tissues in the pelvic region.

Another aspect of the invention involves implantation tools, kits, systems, and methods for use in the implantation of tissue stimulator IMDs (also referred to as tissue stimulators) for delivering tissue stimulation to tissue structures of the pelvic region, e.g., urethral tissue structures, particularly the urethral sphincter and optionally the levator ani, to treat urinary incontinence or anal sphincter structures to treat fecal incontinence. Such tissue stimulators include tissue stimulation IPGs and tissue stimulation leads or simply stimulation leads.

In accordance with one exemplary method of passing a stimulation lead having a stimulation lead body extending from a proximal lead connector end to a distal stimulation electrode through a tissue pathway to dispose the stimulation electrode in or adjacent a selected pelvic tissue structure of a patient, the lead body associated with a lead fixation mechanism extending along at least a portion of the lead body, the method comprising: making a first skin incision through skin inferior to one of the anus or the urethra accessing one of the anal or urethral tissue structures; making at least one second skin incision through the skin in an abdominal region of the patient's body; passing an implantation tool having first and second tool ends through the patient's body between the first and second skin incisions to dispose the first tool end extending from one of the first and second skin incisions; coupling the first tool end to the lead connector end; manipulating the tool to draw the lead body and fixation mechanism through the tissue pathway and the lead connector end out of the other of the first and second skin incisions; and positioning the stimulation electrode in relation to the pelvic tissue structure and the lead fixation mechanism in the tissue pathway to engage body tissue.

The implantation of a tissue stimulator comprising a stimulation lead implanted in accordance with the above steps may further comprise: forming a subcutaneous tissue pocket proximate the abdominal skin incision; coupling a tissue stimulation IPG to the lead connector end; inserting the IPG in the pocket; and closing the pocket.

A still further aspect of the invention involves stimulation leads for placement in the pelvic floor having fixation mechanisms for stabilization of the stimulation electrodes to inhibit dislodgement from a selected stimulation site. In certain embodiments, the fixation mechanisms encourage fibrosis about the lead to chronically stabilize the position of the stimulation lead and/or stimulation electrode(s). In certain embodiments, the fixation mechanisms are isolated from body tissue during routing of the stimulation lead through a tissue pathway and then exposed to body tissue to encourage fibrosis.

In certain embodiments, distal body segments of stimulation lead bodies are shaped to advantageously apply unipolar, bipolar or multi-polar neurostimulation to a pelvic tissue structure of or adjacent the urethra or anus to effect urethral or anal constriction. Typically, the stimulation lead body has a body axis extending distally of the proximal lead connector assembly and a distal body segment extending laterally to the body axis disposing one or more stimulation electrode along the distal body segment. The lead body may be L-shaped or T-shaped or may comprise a flexible band supporting or incorporating one or more stimulation electrode.

Similar kits, systems, and methods may be practiced for use in the implantation of neural stimulator IMDs to apply neural stimulation to a nerve stimulation electrode of a neural lead positioned in proximity to a nerve in the pelvic region to effect neural stimulation.

This summary has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

The present invention will be more fully understood from the following detailed description of the preferred embodiments thereof, taken together with the drawings, in which:

FIG. 13 is a plan view of the tissue stimulation lead of FIG. 3 disposed in a protective sheath of a protective sheath assembly;

FIG. 14 is a schematic view of the advancement of the curved needle distal end through pelvic tissue from the abdominal incision and emerging from the vaginal incision of the female patient to be coupled to a sheath connector of the protective sheath assembly of FIG. 13 to draw it and the enclosed tissue stimulation lead through the tissue pathway in the manner depicted in FIGS. 6-10;

FIG. 15 is a schematic illustration of distal segments of the protective sheath and tissue stimulation lead of FIG. 13 disposed in the tissue pathway to position the tissue stimulation electrode in a selected stimulation site in the urethral tissue structure;

FIG. 19 is a plan view of a bipolar combined tissue stimulation lead and urethral sling having two elongated, generally rectangular, fixation meshes extending along a length of the lead body;

FIG. 20 is a plan view of the tissue stimulation lead and urethral sling of FIG. 19 disposed within a protective sheath assembly;

The drawings are not necessarily to scale.

DETAILED DESCRIPTION OF PREFERRED EMBODIMENTS

For convenience, the expressions "tissue stimulator" and "tissue stimulation" are employed herein to characterize implantable stimulators comprising electrical medical leads and IPGs and the stimulation applied to tissue structures of the abdominopelvic or simply pelvic region to enervate to cause muscle tissues to contract.

Various features and aspects of the present invention may be practiced separately or in combination and may find application in the positioning and fixation of tissue stimulation leads in various parts of the pelvic region to treat various pelvic disorders. The illustrated embodiments depict tissue stimulation electrode positioning and stabilization in urethral tissue structure of a female patient for alleviating urethral incontinence, but the same or similar procedures and/or devices may be employed in electrode positioning and stabilization in urethral tissue structures of a male patient for alleviating urethral incontinence. Moreover, in either male or female patients, the same or similar procedures and/or devices may be employed in electrode positioning and stabilization in other tissues or adjacent the pudendal or sacral nerves for application of neural stimulation to such nerves for treatment of various pelvic disorders described above. Finally, in either male or female patients, the same or similar procedures and/or devices may be employed in electrode positioning and stabilization in anal sphincter and pelvic muscle tissues governing or aiding in maintaining fecal continence.

Exemplary tissue stimulation leads that may be implanted employing implantation tools, kits, systems, and methods of the present invention and coupled to a tissue stimulation IPG are depicted in FIGS. 1-4. Exemplary tools used in and steps of implanting one of the exemplary tissue stimulation leads and coupling the lead connector to a tissue stimulation IPG are depicted in FIGS. 5-9. Further modifications of the tissue stimulation leads and the implantation tools, kits, systems, and methods of the present invention are depicted in the remaining figures.

Figure 1:
FIG. 1 is a plan view of a bipolar tissue stimulation lead.
Figure 2:
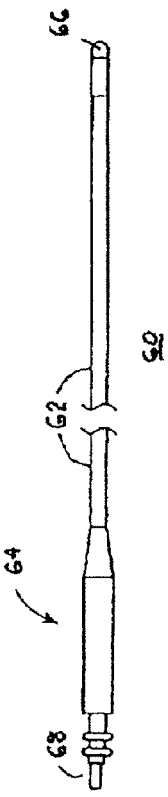
FIG. 2 is a plan view of a unipolar tissue stimulation lead.

In accordance with one aspect of the present invention, conventional multi-polar and unipolar tissue stimulation leads, e.g., the bipolar tissue stimulation lead 50 depicted in FIG. 1 and the unipolar tissue stimulation lead 60 depicted in FIG. 2, respectively, may be implanted employing the implantation tools, kits, systems, and methods of the present invention and coupled to a compatible tissue stimulation IPG as depicted in FIGS. 5-9. The tissue stimulation leads 50 and 60 are operable, when coupled to an IPG, to transmit EMG signals to the IPG sense amplifier (if present in the IPG), and to deliver the stimulation from an IPG output circuit to a stimulation site of the patient's body, particularly the region of the urethra. It will be understood that the term "tissue stimulation electrode" used herein embraces an electrode that is employed to deliver neurostimulation from such an IPG output circuit and to conduct EMG signals to an IPG sense amplifier.

The bipolar tissue stimulation lead 50 comprises an elongated lead body 52 extending from a proximal lead connector assembly 54 comprising spaced apart lead connector elements 53 and 55 to spaced apart, tissue stimulation electrodes 56 and 58, respectively, for bipolar stimulation of tissue at the stimulation site. The lead body 52 is formed of an electrically insulating sheath encasing electrical conductors that extend from the distal electrodes 56 and 58 to connector elements 53 and 55 of the lead connector assembly 54. The distal tissue stimulation electrode 58 may be at or proximate the lead body distal end. The lead connector assembly 54 may conform in size and shape to a conventional bipolar, in-line connector assembly, e.g., conforming to the IS-1 bipolar lead convention.

Similarly, the unipolar tissue stimulation lead 60 comprises an elongated lead body 62 extending from a proximal lead connector assembly 64 to a single tissue stimulation electrode 66 that may be at or proximate the lead body distal end for unipolar stimulation of tissue at the stimulation site. The lead body 62 is formed of an electrically insulating sheath encasing a single electrical conductor that extends from the distal tissue stimulation electrode 66 to a proximal connector element 68 of the lead connector assembly. The lead connector assembly 64 may conform in size and shape to a conventional unipolar, in-line connector assembly, e.g., conforming to the IS-1 unipolar lead convention.

In accordance with a further aspect of the present invention, the lead bodies of conventional unipolar, bipolar and multi-polar tissue stimulation leads, e.g., the bipolar tissue stimulation lead 50 depicted in FIG. 1 and the unipolar tissue stimulation lead 60 depicted in FIG. 2, incorporate fixation mechanisms for stabilization of the tissue stimulation electrodes to inhibit dislodgement from a selected stimulation site. In the depicted embodiments, the fixation mechanisms encourage fibrosis about the lead to chronically stabilize the position of the tissue stimulation lead and/or tissue stimulation electrode(s). The fixation mechanisms may comprise mesh bodies taking a number of forms arranged along the lead body disposed adjacent the tissue stimulation electrode(s) or more proximally along the lead bodies 52 and 62.

Figure 3:
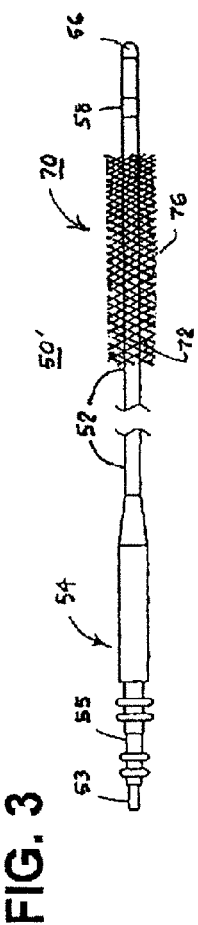
FIG. 3 is a plan view of a bipolar tissue stimulation lead having one or more elongated generally rectangular fixation mesh extending along a length of the lead body.

For example, the bipolar tissue stimulation lead 50' depicted in FIG. 3 comprises one or fixation mechanism 70 extending along and affixed to the lead body 52 intermediate the proximal lead connector assembly 54 and the distal tissue stimulation electrodes 56 and 58. The fixation mechanism 70 may comprise a single, substantially rectangular, sheet of mesh 72 extending along one side of lead body 52 or two substantially rectangular, mesh sheets extending along opposite sides of lead body 52. Alternatively, the fixation mechanism 70 may comprise a cylinder or tube of mesh 72 extending around the circumference of the lead body 52 and affixed thereto. The fixation of the mesh sheet(s) or tube to the lead body 52 may be a continuous along or at intermittent points along a line of contact between the mesh and the lead body 52. The fixation may be effected by adhesion of the mesh 72 to the lead body 52. A similar fixation mechanism 70 may be affixed to the lead body 62 of the unipolar tissue stimulation lead 60. The sheet(s) or tube of mesh 72 may extend continuously as depicted in FIG. 3 or intermittently along a portion of the lead body 52, and may extend to or distally of the tissue stimulation electrodes 56 and 58 and to the lead body distal end.

The side edges 76 of the sheet or sheets of mesh 72 constitute outwardly extending, severed strands of the open pore mesh 72. When the lead 50' is implanted as described below, the side edges 76 and the substantially rectangular, sheet or sheets of mesh 72 may fold inward on contact with the tissue in the tissue pathway. It may be desirable to maintain the substantially rectangular shape of the sheet or sheets of mesh 72 to maximize tissue contact area and tissue ingrowth into the mesh pores. Thus, the mesh 72 may be stiffened in its entirety or along the side edges 76 to maintain the substantially rectangular shape to engage with tissue when drawn through a tissue pathway.

Figure 4:
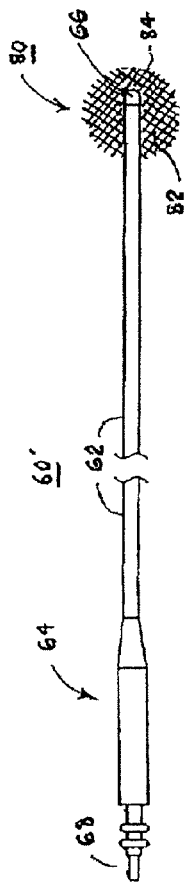
FIG. 4 is a plan view of a unipolar tissue stimulation lead having a generally circular fixation mesh coupled to the lead body and/or distal electrode.

The unipolar lead 60' depicted in FIG. 4 incorporates an alternative fixation mechanism 80 that may be affixed to the lead body 62 at or proximate the lead body distal end. In this example, the fixation mechanism 80 comprises a single, substantially circular, sheet of mesh 82 extending along one side of lead body 62 at the lead body distal end. In the implantation procedure illustrated in FIGS. 5-9, it will be observed that the fixation mechanism 80 is disposed in the tissue structure of the urethra at the target sense/stimulation site that is accessible from an incision accessing the tissue structures of the urethra, e.g., a vaginal incision in the apex of the vagina. Tissue ingrowth into mesh pores of mesh 82 is expected to aid in stabilization of the tissue stimulation electrode(s) 66. In addition, a fixation suture may be placed through a mesh pore mesh 82 and adjacent tissue to provide acute fixation. In this location, it may not be desirable to stiffen the mesh 82 or the mesh edge 84.

The mesh 72, 82 may be knitted of flexible strands of polymers and plastics and any combination of such materials. Commercial examples of such materials include Mersile™, Teflon™, Gore-Tex™, Silastic™, Marlex™, Prolene™, and Vaskutek™ polymers. Other examples of suitable materials include those disclosed in the above-referenced '450 patent. Specific examples of synthetic sling mesh strands include absorbable and non-absorbable materials such as polypropylene, polyethylene, nylon, PLLA and PGA. Additional meshes are disclosed in Dietz et al., "Mechanical Properties of Urogynecologic Implant Materials", *Int. Urogynecol. J.* (2003) 14: 239-243; and Iglesia et al., "The Use of Mesh in Gynecologic Surgery", *Int. Urogynecol. J.* (1997) 8:105-115.

FIGS. 5-9, illustrate one procedure and tools employed in the implantation of the tissue stimulation leads 50, 50', 60, 60' in a pelvic region 10 of a female patient's body in a tissue pathway 86 extending from a neurostimulation site adjacent the urethra 22 to an IPG implantation pocket. The depicted procedure avoids the need to direct the lead body over the pubic bone and difficulties in passing the lead through a short introducer and maintaining the tissue stimulation electrode(s) in the urethral tissue structure of the urethra 22.

The abdominopelvic region 10 of the female patient's body depicted in FIGS. 5-9 is highly simplified for ease of explanation of the procedure, but includes a depiction of the skin 12, the external genitalia 20, a portion of the pelvic girdle 30, and a transobturator nerve 43 and artery 47 traversing a transobturator membrane 42. The external genitalia 20 include the urethral orifice 22 into the urethra 26 and the vaginal orifice 24. Portions of the right and left coxal bones 32 and 34 of the pelvic girdle 30 are illustrated including at least the ischium and pubis, including the superior pubic pubic ramus and the posterior ischiopubic pubic ramus joined at the interpubic disc.

Figure 5:
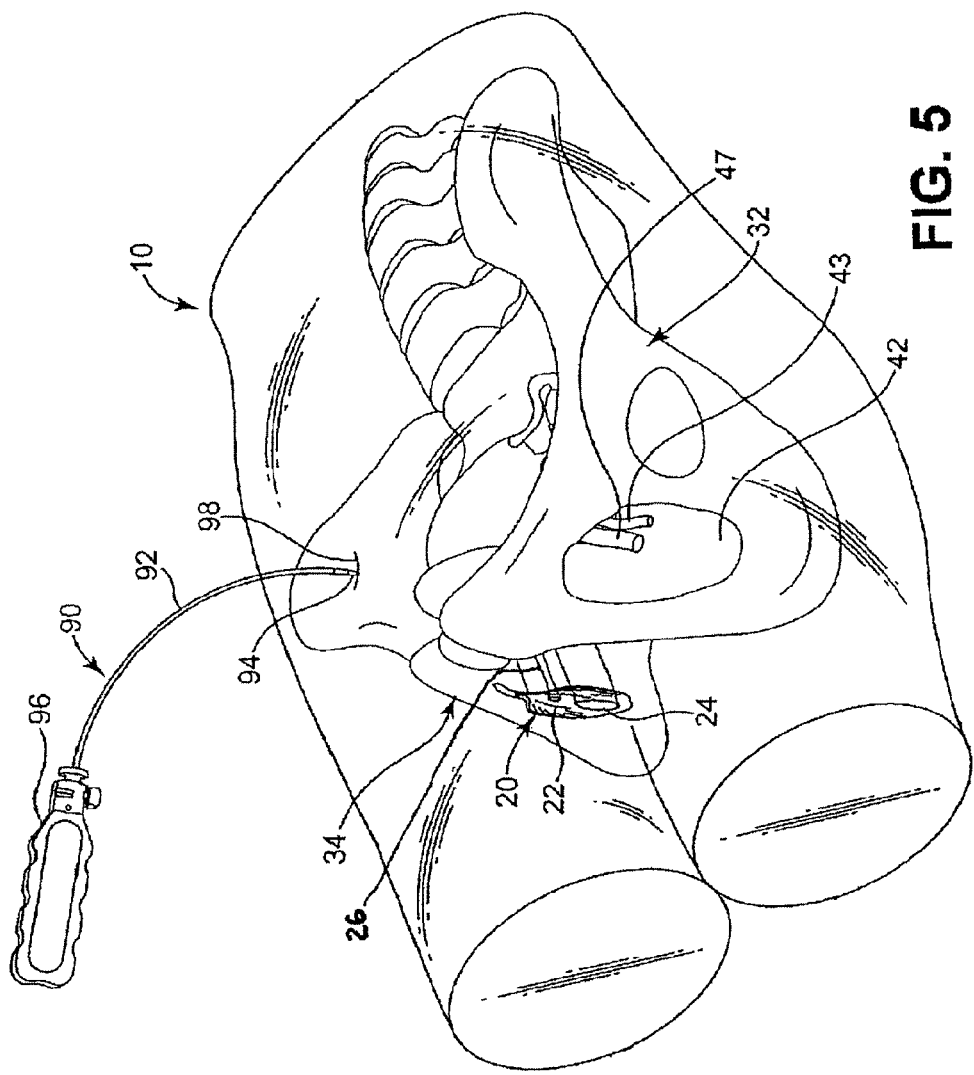
FIG. 5 is a schematic view of the use of a tool having a curved needle to begin the creation a tissue pathway from an abdominal incision toward a vaginal incision of a female patient.

In the initial steps of the procedure illustrated in FIG. 5, a skin incision inferior to the urethra 26, e.g., a vaginal incision, has been made to access and expose a section of the tissue structure around the urethra 26 between the urethral orifice 22 and the vaginal orifice 24 that includes the target tissue structure for neurostimulation. A further abdominal skin incision 98 has been made in the skin 12. A tissue pathway 86 is made therebetween using a lead implantation tool comprising a needle advanced from the skin incision to the abdominal incision as disclosed in the above-referenced U.S. Patent Application Publication No. 2002/0165566 or from the abdominal incision to the skin incision as described in the above-referenced U.S. Patent Application Publication No. 2005/0043580. In either case, the needle has first and second needle ends and is used to form the tissue pathway through the abdominal skin incision, the patient's body, and the vaginal skin incision to dispose the first needle end extending from the skin incision and the second needle end extending from the urethral incision. The lead connector is coupled to the second needle end, and the needle is tool is manipulated to draw the lead body through the tissue pathway and the lead connector end out of the skin incision. The tissue stimulation electrode(s) is positioned in relation to the tissue structure of the urethra, and the lead connector assembly is attached to a tissue stimulation IPG.

In the exemplary procedure illustrated in FIG. 5, a curved lead implantation tool 90 is poised to make a tissue pathway 86 between the skin incision 98 and the vaginal incision. The tissue pathway 86 corresponds to that created in use of the sling implantation tools disclosed in the above-referenced U.S. Patent Application Publication No. 2005/0043580. A similar procedure creating a tissue pathway through a male patient's body from a urethral incision accessing the urethral tissue structure and an abdominal skin incision may be followed to install a tissue stimulation lead disclosed herein to stimulate the urethral tissue structure to alleviate incontinence.

In this example, the lead implantation tool 90 comprises a proximal handle 96, a needle 92 curved in a single plane and extending from the proximal handle 96 to a needle distal end 94. The lead implantation tool 90 can correspond generally to the BioArc™ SP and SPARC™ single use sling implantation tools sold by American Medical Systems, Inc., in a kit with an elongated urethral sling and used to implant the sling extending through right and left tissue pathways and around the urethra 26. Such elongated, self-fixating, urethral slings are implanted for treating female prolapse employing a pair of sling implantation instruments or tools like lead implantation tool 90. The sling implantation tools each comprise a handle with an elongated needle portion terminating in a needle distal end adapted to be coupled to a free ends of the urethral sling. The sling implantation tools may have mirror image, right and left handed, needle shapes.

Figure 6:
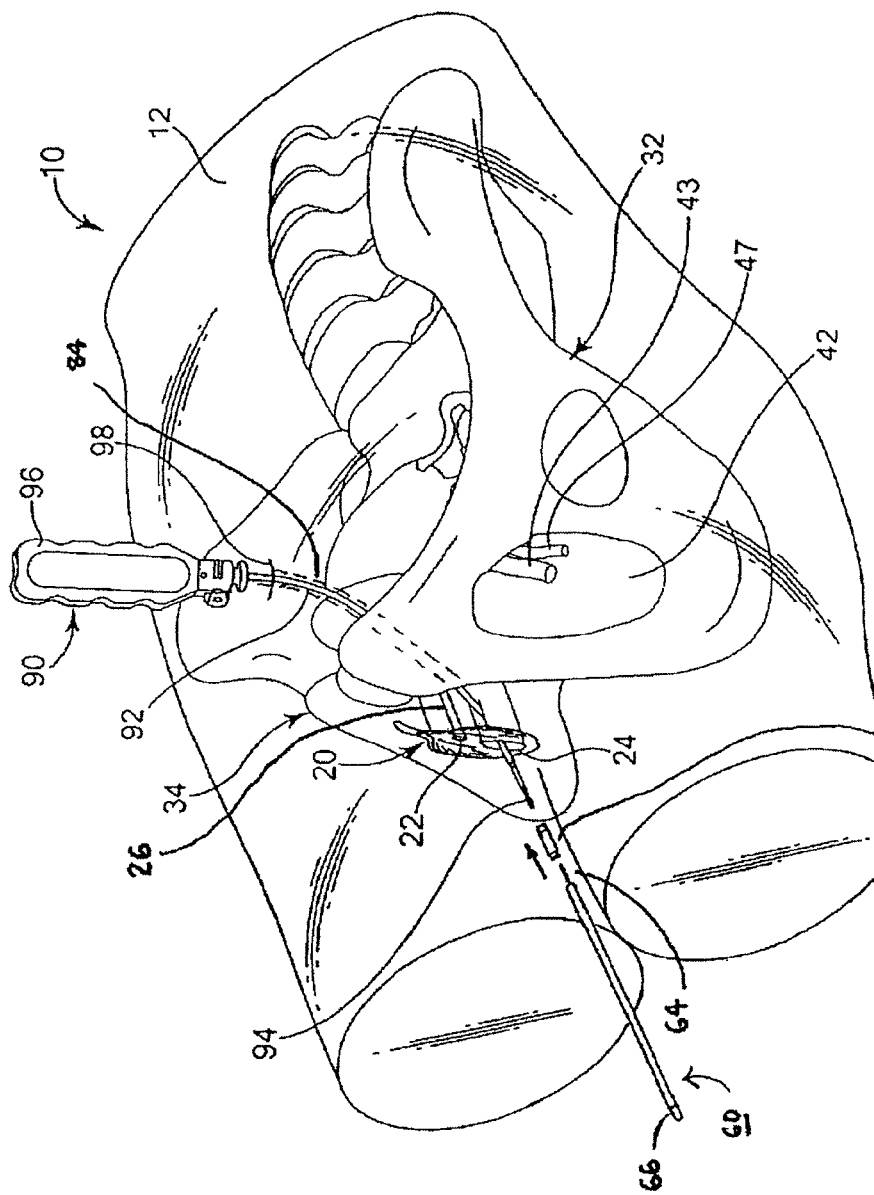
FIG. 6 is a schematic view of the advancement of the curved needle distal end through pelvic tissue from the abdominal incision and emerging from the vaginal incision of the female patient to be coupled to a lead connector of one of the tissue stimulation leads of FIGS. 1-4, e.g., the tissue stimulation lead of FIG. 2.

In the practice of the illustrated procedure, only a single lead implantation tool 90 is employed to create a single right hand or left hand pathway 86 as illustrated in FIG. 6. The needle distal end 94 may be shaped to engage the particular shape and dimensions of at least a proximal portion of the lead connector assemblies 54 and 64. Alternatively, a connector 88 depicted in FIGS. 6-8 may be provided for temporarily connecting the needle distal end 94 with at least a proximal portion of the lead connector assemblies 54 and 64. The connector 88 may simply comprise an elastomeric tube having axially aligned lead connector and needle distal end lumens sized and shaped to provide interference fits with the respective lead connector pins 53 and 68 inserted into the lead connector lumen and the needle distal end 94 inserted into the needle distal end lumen.

Figure 7:
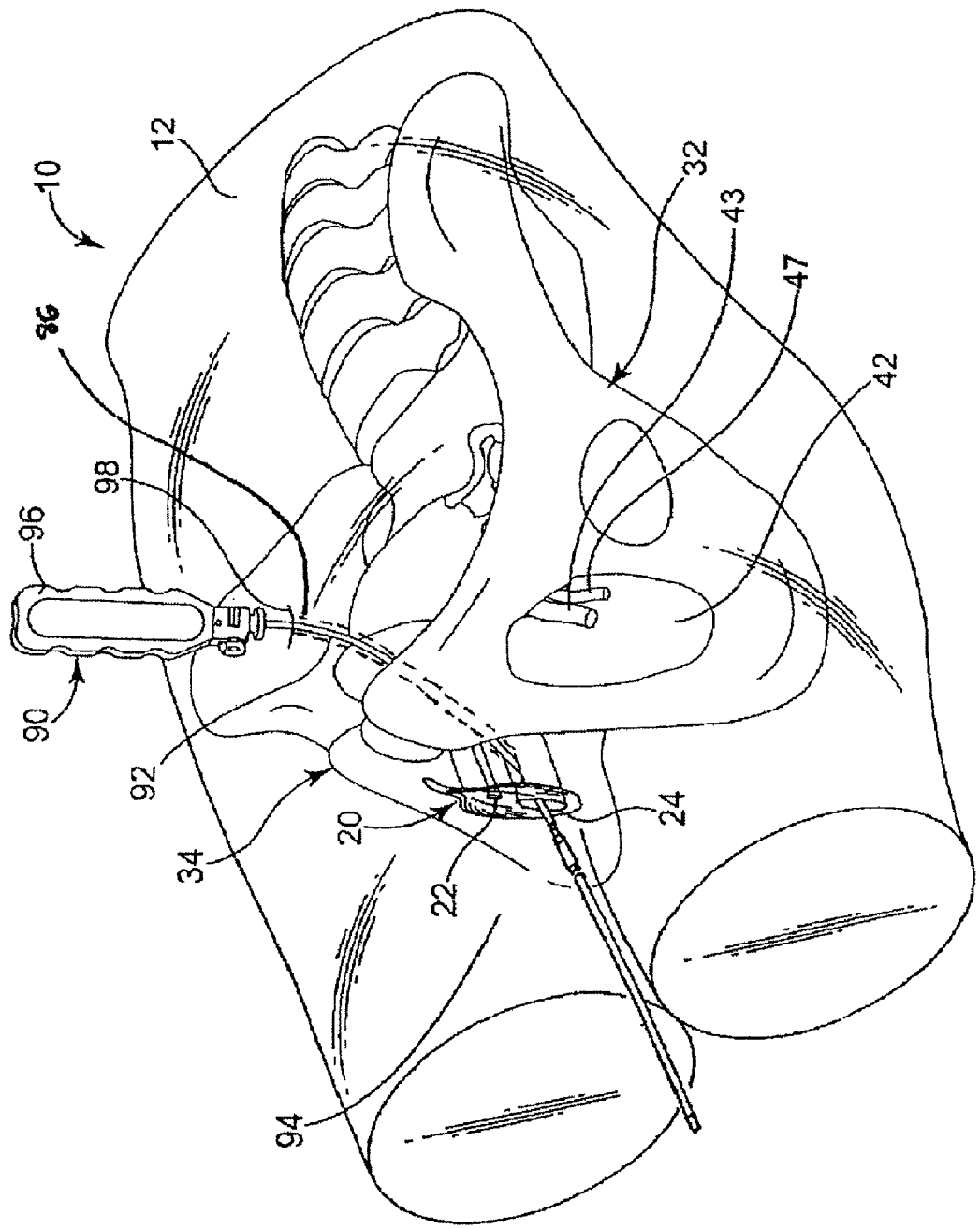
FIG. 7 is a schematic view of the attachment of a tissue stimulation lead connector of a tissue stimulation lead of one of FIGS. 1-4, e.g., the tissue stimulation lead of FIG. 2, to the needle distal end to draw the tissue stimulation lead through the tissue pathway.
Figure 8:
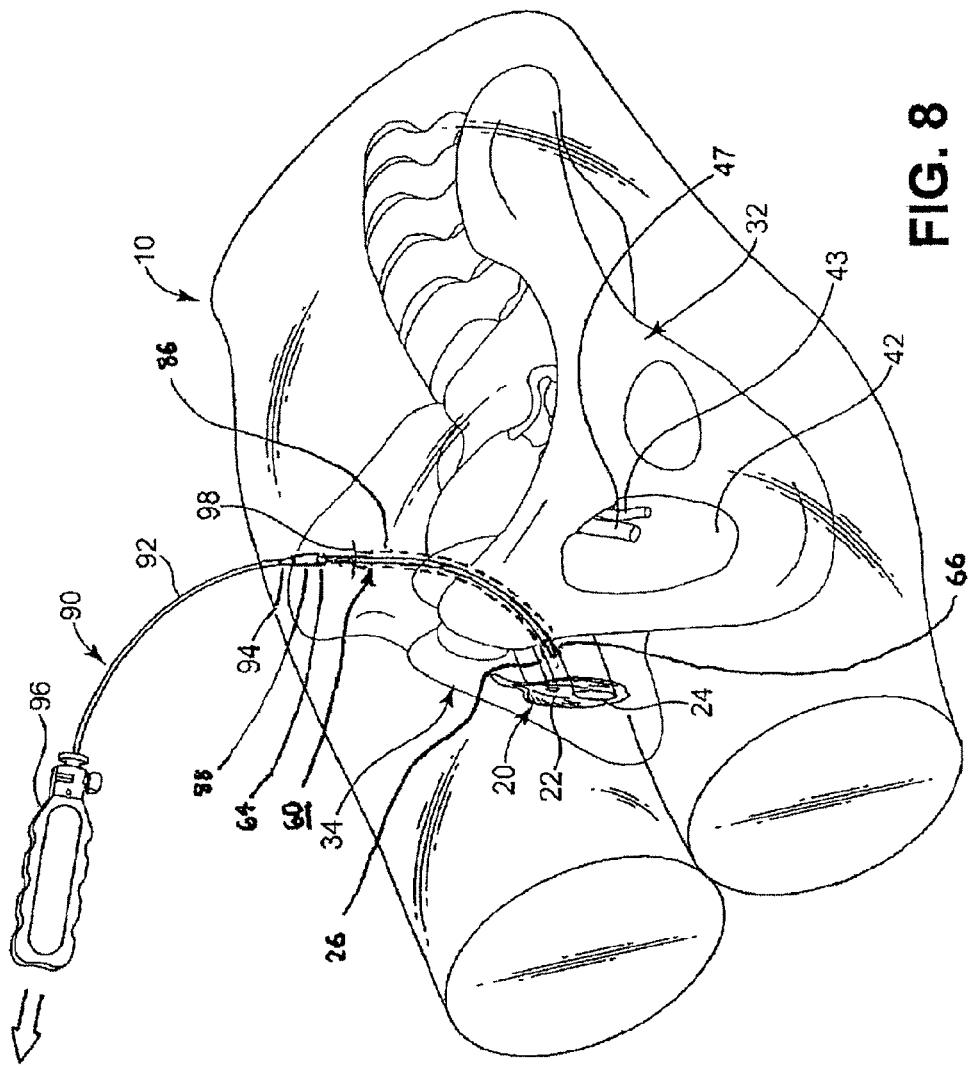
FIG. 8 is a schematic view of the tissue stimulation lead of one of FIGS. 1-4, e.g., the tissue stimulation lead of FIG. 2, drawn through the tissue pathway to dispose the tissue stimulation electrode in a selected stimulation site in the urethral tissue structure and the lead connector out of the abdominal incision.

The implantation of the simplest unipolar lead 60 through the tissue pathway 86 created by the needle 92 is illustrated in FIGS. 6-8 for ease of illustration. It should be noted that the tissue pathway 86 created by needle 92 and traversed by lead body 62 is interior to the depicted right coxal bone 32 as shown in FIGS. 6 and 7 and disclosed more completely in the instructions for use of the BioArc™ SP and SPARC™ single use sling implantation tools and in the above-referenced U.S. Patent Application Publication No. 2005/0043580. The pathway 86 and lead body 62 are exposed through the coxal bone 32 for ease of view in FIGS. 8 and 9.

The attachment of the tissue stimulation lead connector 64 of tissue stimulation lead 60 to the needle distal end 94 to draw the tissue stimulation lead 60 through the tissue pathway is illustrated in FIG. 7 The retraction of the tool handle 96 and needle 92 to draw the tissue stimulation lead 60 through the tissue pathway to dispose the tissue stimulation electrode 66 in a selected stimulation site in the urethral tissue structure adjacent the urethra 26 and the lead connector assembly 64 out of the abdominal incision 98 is illustrated in FIG. 8. For example, the electrode 66 may be positioned in relation to the patient's levator ani muscle, which supports and reinforces the operation of the urethral sphincter. The lead connector assembly 64 is detached from the connector 88 and coupled to test equipment or to the tissue stimulator IPG 100 so that stimulation threshold tests may be conducted to assess the efficacy of stimulation and tests of the ability to sense a useful EMG signal may be conducted. Electrode 66 may be repositioned to improve stimulation response and sensing capability.

Figure 9:
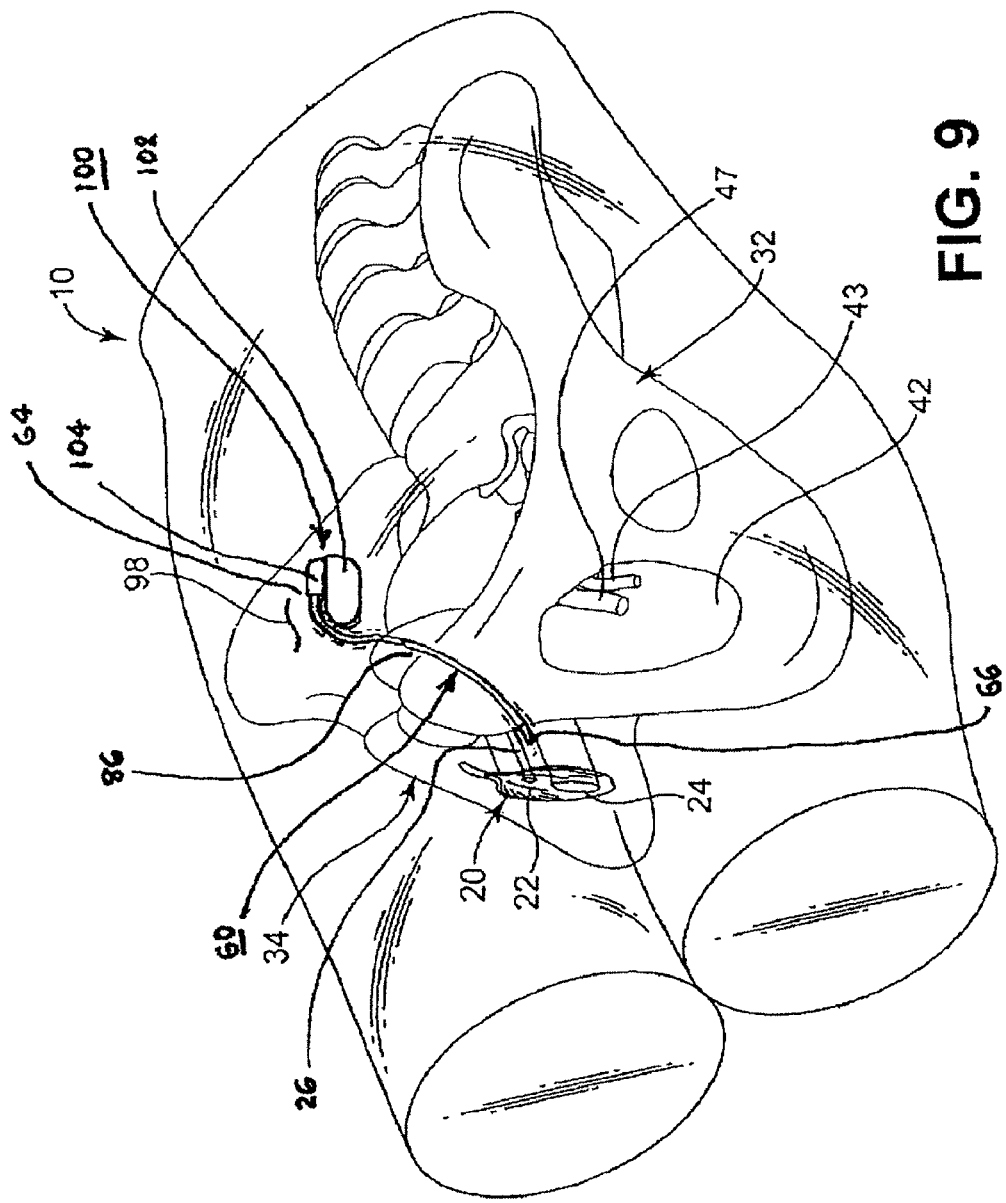
FIG. 9 is a schematic view of the tissue stimulation lead of one of FIGS. 1-4, e.g., the tissue stimulation lead of FIG. 2, drawn through the tissue pathway to dispose the tissue stimulation electrode in a selected stimulation site in the urethral tissue structure and with lead connector coupled to an IPG implanted in a subcutaneous abdominal tissue pocket.

In reference to FIG. 9, the IPG 100 includes a battery, circuitry, and other components in a hermetically sealed housing 102 and a connector header 104 coupled to housing 102. The lead connector assembly 64 is obscured from view as it is inserted into a connector bore of connector header 104. The connector bore accesses IPG connector elements that conform to the same standard as the lead connector assembly 64 to make secure electrical connection with connector pin 68 of the lead 60.

The IPG 100 is adapted to be implanted in a subcutaneous abdominal tissue pocket formed adjacent skin incision 98 and operated to deliver electrical stimulation pulses between electrode 66 and an indifferent electrode formed on the IPG housing 102 to stimulate nerves and muscle tissue structure adjacent the urethra 26 to treat or prevent urge incontinence. The IPG 100 is operable to generate neurological stimulation that may comprise an electrical pulse having a pulse amplitude, shape and width known in the art or a train of a number of such electrical pulses separated by a constant or variable interval between each pulse of the pulse train. These pulse parameters are preferably programmable. The IPG 100 may include an EMG sense amplifier and may have the further functions and attributes of the IPG disclosed in the above-referenced '651 patent and in U.S. Patent Application Publication 2005/0216069. The functions of the IPG 100 and the sensing parameters and stimulation pulse or pulse train parameters, including the interval between stimulation application, may be programmable employing uplink and downlink telemetry transmissions exchanged with an external medical device or programmer in a manner well known in the art.

Figure 10:
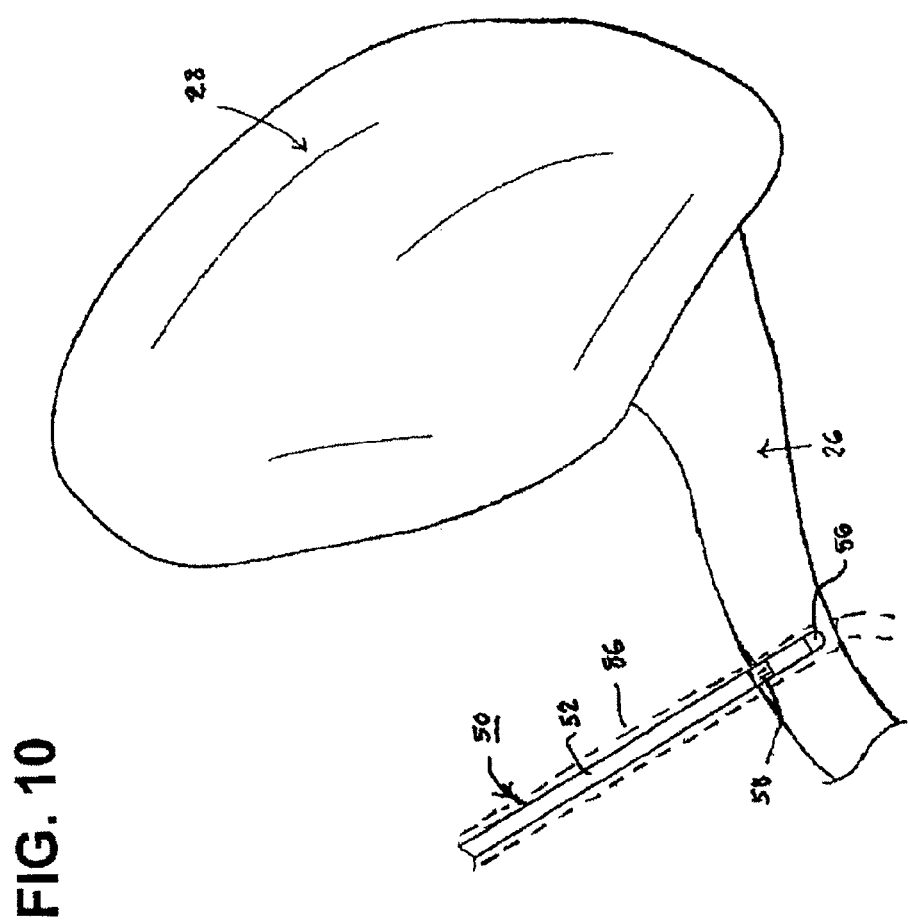
FIG. 10 is a schematic illustration of a distal segment of the tissue stimulation lead of FIG. 1 disposed in the tissue pathway to position the tissue stimulation electrode in a selected stimulation site in the urethral tissue structure.
Figure 11:
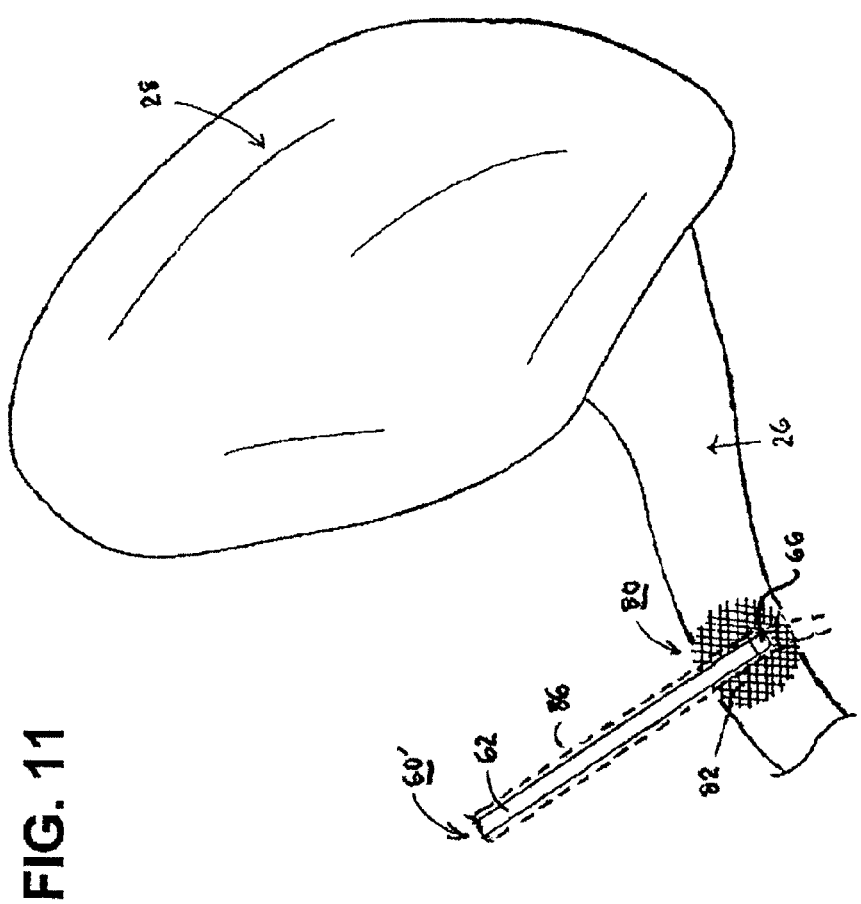
FIG. 11 is a schematic illustration of a distal segment of the tissue stimulation lead of FIG. 4 disposed in the tissue pathway to position the tissue stimulation electrode in a selected stimulation site in the urethral tissue structure.
Figure 12:
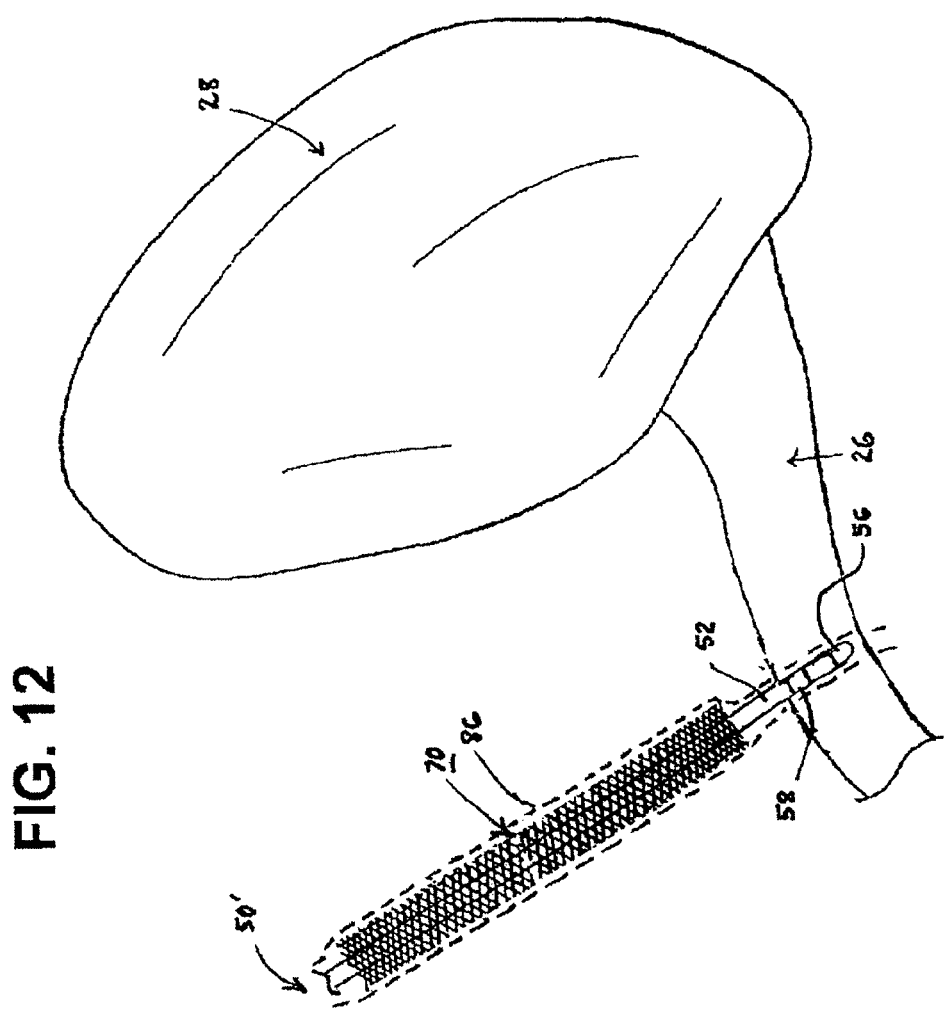
FIG. 12 is a schematic illustration of a distal segment of the tissue stimulation lead of FIG. 3 disposed in the tissue pathway to position the tissue stimulation electrode in a selected stimulation site in the urethral tissue structure.

The procedure illustrated in FIGS. 5-9 may also be employed to implant the unipolar lead 60' and connect it with the IPG 100 or to implant the bipolar leads 50 and 50' and couple their proximal connector assembly 54 with a bipolar IPG. The disposition of the distal portion of the bipolar lead 50 through the tissue pathway 86 with the distal tissue stimulation electrodes 56 and 58 adjacent the urethra 26 and bladder 28 is schematically illustrated in FIG. 10. Similarly, the disposition of the distal portion of the unipolar lead 60' through the tissue pathway 86 with the distal tissue stimulation electrode 66 and fixation mechanism 80 adjacent the urethra 26 and bladder 28 is schematically illustrated in FIG. 11. The disposition of the distal portion of the bipolar lead 50' through the tissue pathway 86 with the distal tissue stimulation electrodes 56 and 58 adjacent the urethra 26 and bladder 28 and the fixation mechanism 70 extending along the tissue pathway 86 is schematically illustrated in FIG. 12.

In a further aspect of the invention depicted in FIGS. 13-16, it may be desirable to provide a protective sheath assembly 110 that encloses the tissue stimulation lead 50' or a unipolar version thereof during implantation through the tissue pathway 86. The protective sheath assembly 110 comprises a proximal sheath connector 112 coupled to a sheath 114 that extends to a sheath distal end 116.

The sheath connector 112 may be formed of a rigid plastic material having an axial bore shaped to receive and interconnect with the needle distal end 94 and shaped to dilate the tissue pathway 86 as the protective sheath assembly 110 and tissue stimulation lead 50' are drawn through the tissue pathway 86. The sheath connector may be shaped to engage the lead connector assembly 54 within the sheath 114.

The sheath 114 may be constructed of a flexible thin transparent plastic film that enables visual examination of the tissue stimulation lead 50' and is sufficiently lubricious that it passes easily through the tissue passageways. The sheath 114 extends a length sufficient to cover the retention mechanism 70 and optionally the tissue stimulation electrodes 56 and 58 terminating in a sheath distal end 116 that may be open. The sheath 11 helps to prevent curling or compression of the mesh 72 of the retention mechanism 70 against the lead body 52 while the lead 50' is pulled through the tissue pathway 86 as described above.

The coupling of the sheath connector 112 to the needle distal end 94 is depicted in FIG. 14. The protective sheath assembly 110 is pulled through the tissue pathway 86 in the manner depicted in FIGS. 7 and 8 and described above to dispose the sheath connector 112 and the lead connector assembly 54 outside the patient's body 10.

Figure 16:
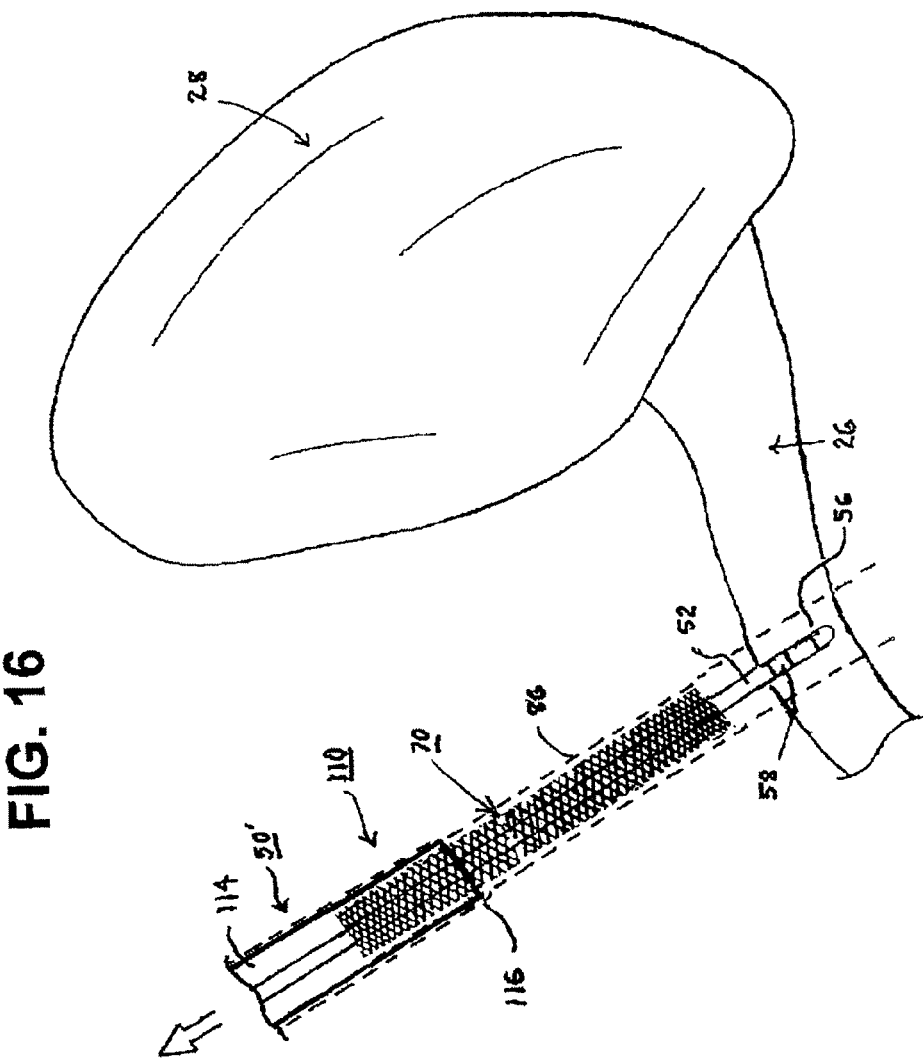
FIG. 16 is a schematic illustration of the withdrawal of the protective sheath over the tissue stimulation lead of FIG. 13 and through the tissue pathway to expose the fixation mechanism to body tissue to enable tissue ingrowth into mesh pores.

At this point, the sheath 114 remains disposed over the retention mechanism 70 through the tissue pathway 86 with the distal tissue stimulation electrodes 56 and 58 adjacent the urethra 26 and bladder 28 as schematically illustrated in FIG. 15. The tissue stimulation electrodes 56 and 58 or the lead distal end may be grasped with an instrument introduced through the vaginal incision to hold the tissue stimulation lead 50' steady as the sheath assembly proximal end is grasped and pullout out through the skin incision 98 as shown in FIG. 16. The lead body 50' remains in the position described above with respect to FIG. 12, with the mesh 72 extending across the enlarged pathway 86 so that tissue ingrowth through the mesh pores is optimized for enhanced electrode stabilization.

The functions of a urethral sling may advantageously be combined with the tissue stimulation leads of the present invention for treating stress urinary incontinence (SUI) diagnosed with urethral hypermobility or intrinsic sphincter deficiency in both men and women. The combined tissue stimulation lead and urethral sling or variations of it can be implanted to treat SUI or other urological disorders, such as urge incontinence, mixed incontinence, overflow incontinence, functional incontinence, prolapse (e.g. vaginal), enteroceles (e.g. of the uterus), rectoceles and other non-urological disorders.

In certain embodiments of this aspect of the invention, the lead bodies 52 and 62 of tissue stimulation leads 50, 50', 60, and 60' are extended distally from the tissue stimulation electrodes 56 and 66 a length substantially the same as the length of lead bodies 52 and 62 terminating in a further connector for making a connection with a needle distal end 94. A fixation mechanism, e.g., fixation mechanism 70, is coupled to the extended lead body to enhance chronic stabilization. A segment of the extended lead body just distal to the tissue stimulation electrodes 56 or 66 may constitute a urethral support portion formed of mesh. It will also be appreciated that the central support portion may be formed of a strip of biocompatible material suitable for chronic implantation that may or may not be resorbable during chronic implantation. Possible materials include allografts, homografts, heterografts, autologous tissues, cadaveric fascia and fascia lata.

The elongated combined urethral sling and tissue stimulation lead assembly may be implanted in any of the above-described manners employing various delivery systems configured for and techniques that involve using right and left hand tools to form right and left transvaginal, transobturator, supra-pubic and pre-pubic tissue pathways. For example, the left hand tissue pathway 86 may be formed using tool 90 as depicted in FIG. 5, and a mirror image right hand tissue pathway may be formed extending from a further skin incision to the vaginal incision employing a right hand tool.

Figure 17:
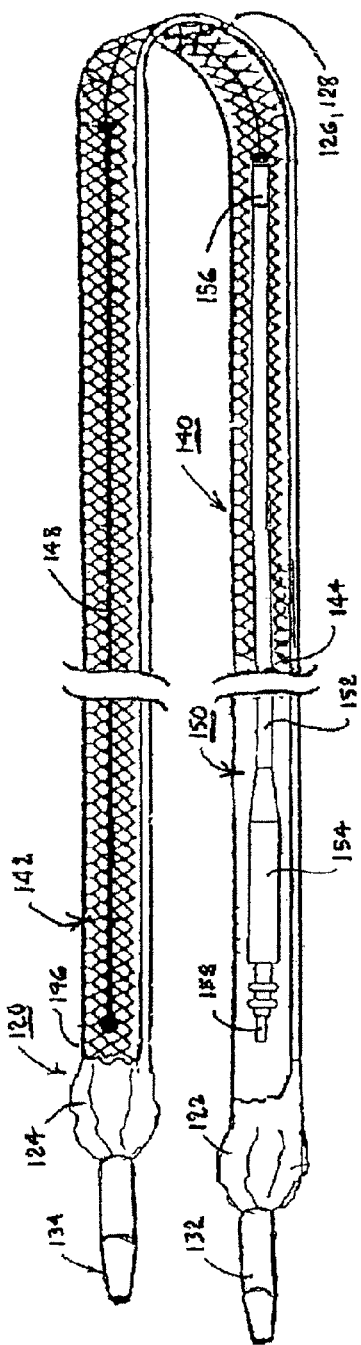
FIG. 17 is a plan view of a combined sling and tissue stimulation lead assembly combining a unipolar tissue stimulation lead with a sling mesh within a protective sheath assembly.
Figure 18:
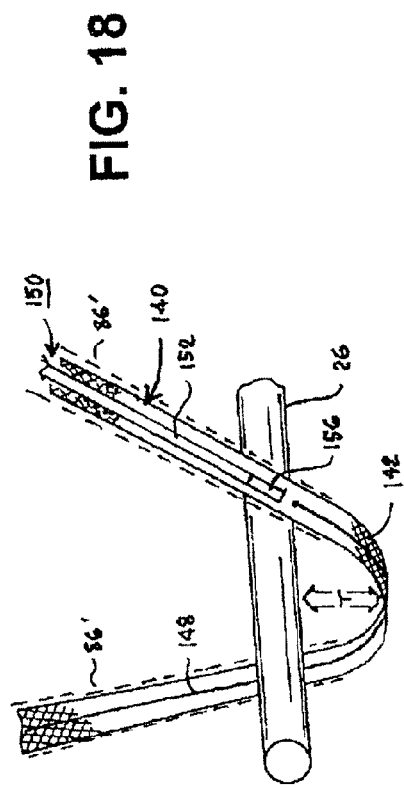
FIG. 18 is a schematic illustration of the positioning of a portion of the combined sling and tissue stimulation lead assembly of FIG. 17 disposed through right and left tissue pathways and around the urethra to position a tissue stimulation electrode in the urethral tissue structure adjacent the urethra, the sling stabilizing the tissue stimulation electrode and supporting the urethra.

It will be appreciated that a protective sheath assembly may be advantageously provided to contain a combined sling and tissue stimulation lead assembly as depicted in FIGS. 17 and 18, for example. In this example, the combined sling and tissue stimulation lead assembly 140 is encased within the protective sheath assembly 120.

The protective sheath assembly 120 comprises protective sheathes 122 and 124 extending from sheath end connectors, 132 and 134, respectively to free and open sheath ends 126 and 128, respectively. The open sheath ends 126 and 128 may be overlapped for a short distance. Preferably, the protective sheathes 122 and 124 are constructed of a flexible thin transparent plastic film that enables visual examination of the combined sling and tissue stimulation lead assembly 140 and that is sufficiently lubricious that it passes easily through the tissue passageways of the patient formed using the right hand and left hand sling implantation tools of the types described above or otherwise created. The sheathes 122 and 124 can include sheath indicia or tear scores, perforations or holes for assisting the surgeon in properly orienting the combined sling and tissue stimulation lead assembly 140 relative to the urethra.

The combined sling and tissue stimulation lead assembly 140 includes an elongated mesh 142 and the unipolar tissue stimulation lead 150. The tissue stimulation lead 150 comprises elongated lead body 152 extending from a proximal lead connector assembly 154 to a single tissue stimulation electrode 156 that may be at or proximate the lead body distal end for unipolar stimulation of tissue at the stimulation site. The lead body 152 is formed of an electrically insulating sheath encasing a single electrical conductor that extends from the distal tissue stimulation electrode 156 to a proximal connector element 158 of the lead connector assembly 154. The lead connector assembly 154 may conform in size and shape to a conventional unipolar, in-line connector assembly, e.g., in conformance with the IS-1 unipolar lead convention.

The elongated mesh 142 extends from a first mesh end 144 to a second mesh end 146 within the sheaths 122 and 124. A segment of the elongated mesh 142 within sheath 122 extends along, and is adhered to or attached to, a distal segment of the lead body 152. The elongated mesh 142 continuously extends from the lead distal end and tissue stimulation electrode 156 through the sheath 124 to the sheath end connector 134 that sheath 124 is attached to. At least one tension control element or inelastic tensioning suture 148 extends from one suture end attached to the mesh 142 proximate the sling end connector 124 to a second suture end attached to the mesh proximate the tissue stimulation electrode 156, for example. The tensioning suture 148 may take the forms of and be tied or otherwise attached to the strands of the mesh at the suture ends and at tie points along the length of the tensioning suture 148 as disclosed in the above-referenced '450 patent.

In use, as schematically depicted in FIG. 18, segments of the mesh 142 are disposed in the right and left tissue pathways 86 and 86' of the patient's body to position the tissue stimulation electrode at the target sense/stimulation site that includes the target tissue structure for neurostimulation adjacent the urethra 26 and is accessible from a vaginal incision. The central support portion of the mesh 142 can apply tension T to the urethra 26.

As noted above, the implantation procedure may employ any of the known tools to form the tissue pathways 86 and 86', and the right and left hand tool needle ends may be coupled to the sheath connector ends 132 and 134 to draw the sheaths 122 and 124 and end portions of the combined sling and tissue stimulation lead assembly 140 through the tissue pathways. When both sheath end connectors 132 and 134 are disposed outside the skin incisions, the mesh 142 and sheath 124 are severed from the end connector 134, and the sheath 124 is withdrawn from the skin incision. Similarly, any connection between the sheath end connector 132 and the lead connector assembly 154 is severed, which may also sever the sheath 122 from the end connector 132. Otherwise, the end connector 132 and attached sheath 122 are withdrawn from the incision.

The above-described electrical tests are then conducted to determine the proper positioning of the tissue stimulation electrode 156. Tests are also conducted to determine the proper tension T to apply to the urethra 26. The lead connector assembly 154 is coupled to the IPG 100 and the IPG 100 is disposed in the subcutaneous pocket as described above with respect to FIG. 9. The vaginal and skin incisions to pathways 86 and 86' are closed as described above.

It will be appreciated that a bipolar or multipolar tissue stimulation lead may be substituted for the unipolar tissue stimulation lead 150 in the combined sling and tissue stimulation lead assembly 140 described above. In such a modification, it will be realized that the lead body may be extended so that the distal tissue stimulation electrodes are separated apart a distance enabling positioning of electrodes around the urethra, e.g., one electrode on one side of the urethra and the other electrode on the other side of the urethra.

Figure 21:
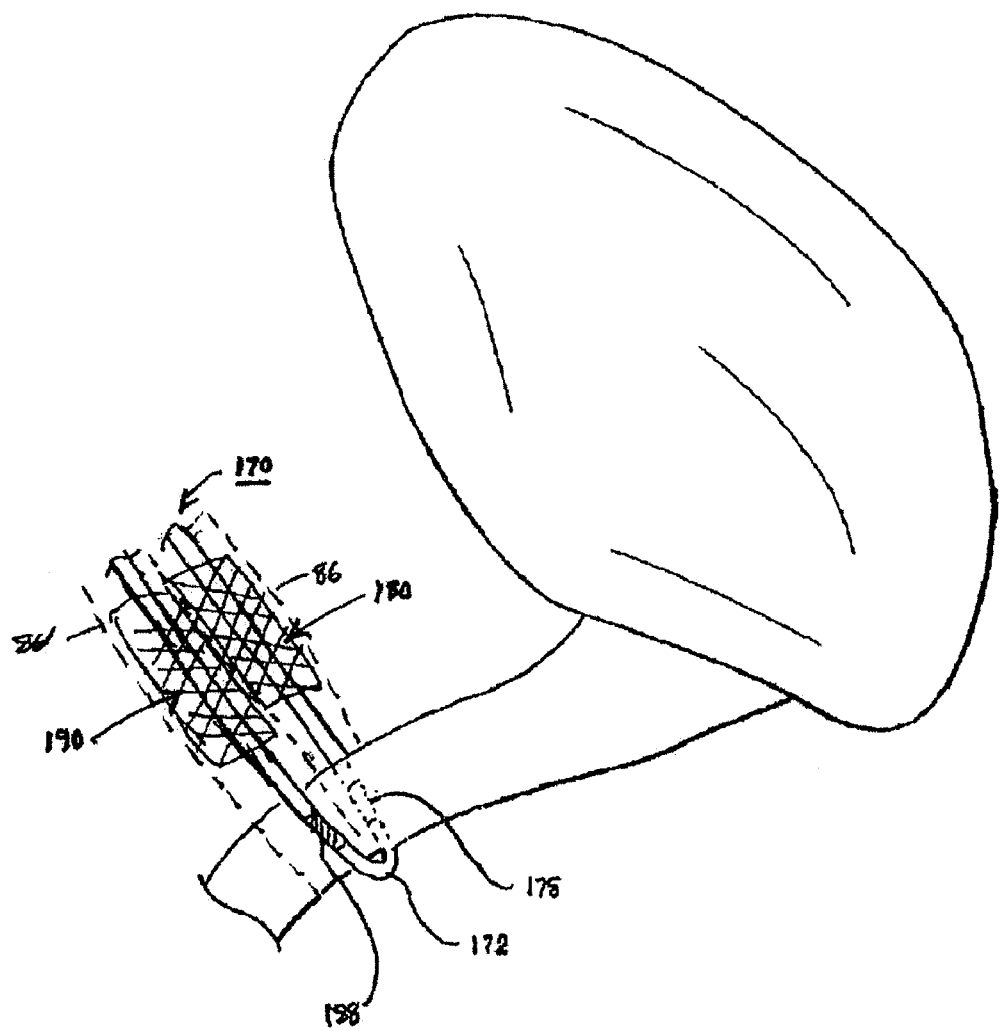
FIG. 21 is a schematic illustration of a portion of the bipolar combined tissue stimulation lead and urethral sling of FIGS. 19 and 20 disposed in relation to the urethra to apply stimulation to and support the urethra.

A further, bipolar, combined sling and tissue stimulation lead assembly 160 is depicted in FIGS. 19-21 that is configured alternatively to enable positioning of a first and second tissue stimulation electrodes on generally opposite sides of the urethra. In this example, the combined sling and tissue stimulation lead assembly 160 includes bipolar tissue stimulation lead 170 that is also encased within the protective sheath assembly 120.

As depicted in FIGS. 19-21, the bipolar tissue stimulation lead 170 comprises an elongated lead body 172 extends from a first proximal lead connector assembly 174 to a first tissue stimulation electrode 178, then to a second tissue stimulation electrode 188, and then to a second proximal lead connector assembly 184. The lead body 172 is formed of an electrically insulating sheath encasing a first electrical conductor that extends from the first tissue stimulation electrode 178 to a first connector element 176 of the first lead connector assembly 174 and encasing a second electrical conductor that extends from the second tissue stimulation electrode 188 to a second connector element 186 of the second lead connector assembly 184.

The lead connector assemblies 174 and 184 may conform in size and shape to a conventional unipolar, in-line connector assembly, e.g., in conformance with the IS-1 unipolar lead convention. In this instance, the IPG 100 would have a connector header 104 having side-by-side connector bores and connector elements conforming to the same convention to receive the lead connector assemblies 174 and 184.

In this embodiment, a first fixation mechanism 180 is adhered or attached to segments of the lead body 172 extending between the first lead connector assembly 174 and the first tissue stimulation electrode 178. Similarly, a second fixation mechanism 190 is adhered or attached to a second segment of the lead body 172 extending between the second lead connector assembly 184 and the second tissue stimulation electrode 188. The first and second fixation mechanisms 180 and 190 are formed of generally rectangular sheets of mesh 182 and 192, respectively.

It will be understood that the first and second fixation mechanisms 180 and 190 may be extended along the segment of the lead body 172 extending between the first and second tissue stimulation electrodes 178 and 188, whereby the generally rectangular sheets of mesh 182 and 192 are joined together. In such a variation, it may be possible to eliminate the segment of the lead body 172 extending between the first and second tissue stimulation electrodes 178 and 188. It will also be appreciated that the tissue stimulation electrodes 178 and 188 may take any of the forms and numbers as disclosed below in reference to FIGS. 26-29.

Referring to FIG. 21, it will be understood that the lead body 172 and first and second fixation mechanisms 180 and 190 are adapted to be extended through right and left tissue pathways 86 and 86' in the patient's body and around the urethra 26 following the procedure described above with respect to FIGS. 17 and 18. The procedure results in positioning the first tissue stimulation electrode 178 in the urethral tissue structure on one side of the urethra 26 and positioning the second tissue stimulation electrode 188 in the urethral tissue structure on the other side of the urethra 26. The segment of the lead body 172 extending between the first and second tissue stimulation electrodes 178 and 188 (or any alternative structure) provides a support function for the urethra 26 in the manner described above with respect to FIG. 18.

In the above-described embodiments, the protective sheaths are relatively thin-walled, highly flexible and shaped with a substantially oval cross-section to encase the lead body and the substantially rectangular fabric-like mesh fixation mechanisms. Further embodiments of this aspect of the present invention are realized employing a somewhat more rigid sheath that may have a different cross-section to encase the lead body and active or passive fixation mechanisms during positioning in the tissue pathway 86' and/or 86.

For example, certain embodiments may comprise sheet-like, passive fixation mechanisms that are adapted to be wound under tension into a spiral roll in a reduced spiral cross-section dimension during passage into the tissue pathway 86' and/or 86, e.g. through the lumen of a protective catheter taking the place of the sheath. The spiral roll self-expands under spring force when the fixation mechanisms are released from the catheter lumen. For convenience such fixation mechanisms are referred to as spiral fixation mechanisms.

Figures 22A, 22B:
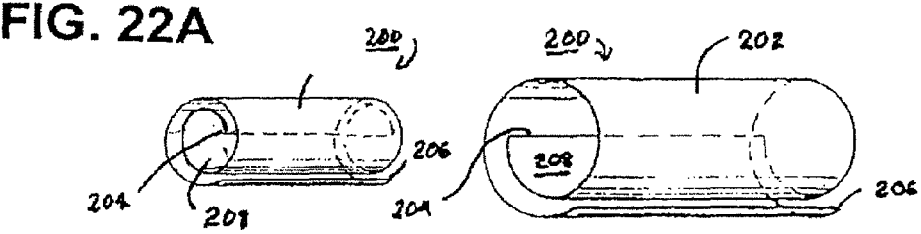
FIGS. 22A and 22B are schematic views of a generic spiral fixation mechanism for use in stabilizing tissue stimulation leads in body pathways.

An exemplary, generic spiral fixation mechanism 200 is depicted in a compressed state in FIG. 22A and an expanded state in FIG. 22B. The spiral fixation mechanism 200 comprises a sheet 202 wound into the tubular configuration extending from an inner side 204 to an outer side 206 and defining a spiral lumen 208. The spiral lumen 208 has a diameter somewhat larger than the lead body diameter. A portion of the inner surface of sheet 202 along the inner side would be affixed or adhered to the lead body (not shown) extending through the spiral lumen 208.

Figures 23A, 23B:
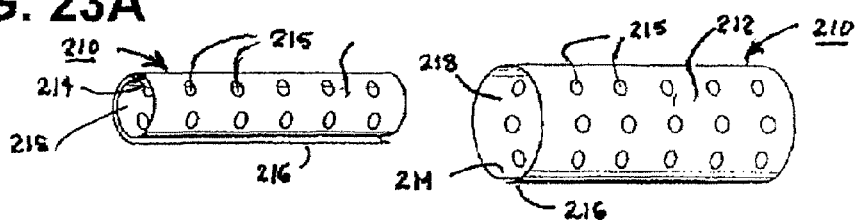
FIGS. 23A and 23B are schematic views of a perforated spiral fixation mechanism for use in stabilizing tissue stimulation leads in body pathways.

The spiral fixation mechanism 210 depicted in FIGS. 23A and 23B comprises a perforated sheet 212 wound into the tubular configuration extending from an inner side 214 to an outer side 216 and defining a spiral lumen 218. The spiral lumen 218 has a diameter somewhat larger than the lead body diameter. A portion of the inner surface of sheet 212 along the inner side would be affixed or adhered to the lead body (not shown) extending through the spiral lumen 218. The sheet 212 is perforated with multiple perforations 215 to allow tissue ingrowth through the sheet 212.

Figures 24A, 24B:
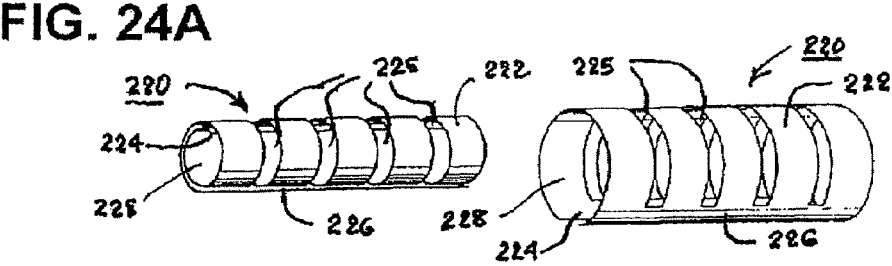
FIGS. 24A and 24B are schematic views of a perforated spiral fixation mechanism for use in stabilizing tissue stimulation leads in body pathways.

The spiral fixation mechanism 220 depicted in FIGS. 24A and 24B comprises a perforated sheet 222 wound into the tubular configuration extending from an inner side 224 to an outer side 226 and defining a spiral lumen 228. The spiral lumen 228 has a diameter somewhat larger than the lead body diameter. A portion of the inner surface of sheet 222 along the inner side would be affixed or adhered to the lead body (not shown) extending through the spiral lumen 228. The sheet 222 is perforated with multiple slits 225 to allow tissue ingrowth through the sheet 222.

Figures 25A, 25B:
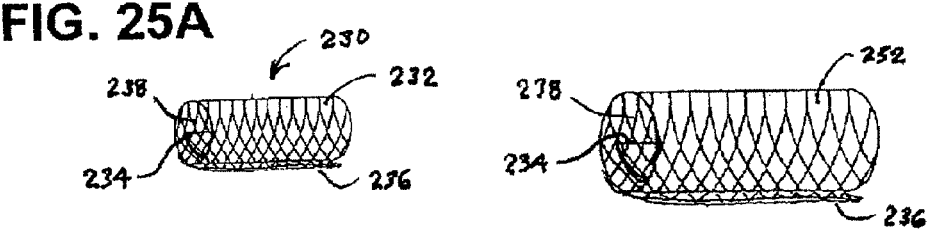
FIGS. 25A and 25B are schematic views of a perforated spiral fixation mechanism for use in stabilizing tissue stimulation leads in body pathways.

The spiral fixation mechanism 230 depicted in FIGS. 25A and 25B comprises a perforated sheet 232 wound into the tubular configuration extending from an inner side 234 to an outer side 236 and defining a spiral lumen 218. The spiral lumen 238 has a diameter somewhat larger than the lead body diameter. A portion of the inner surface of sheet 232 along the inner side would be affixed or adhered to the lead body (not shown) extending through the spiral lumen 238. The sheet 232 is preferably formed of a mesh or in a stent-like configuration that self expands and wherein the mesh pores 235 or apertures 215 between stent struts allow tissue ingrowth through the sheet 232.

In use, the spiral fixation mechanism 200, 210, 220, 230 is inserted into a catheter lumen of a delivery catheter substituted for the above-described sheaths or otherwise held in the compressed state around the lead body. The spiral fixation mechanisms 200, 210, 220, 230 self-expand under spring force when they are released from the catheter lumen.

Turning to FIGS. 26-29, tissue stimulation electrodes in distal segments of further exemplary tissue stimulation leads are depicted in relation to the schematically depicted urethra 26 and bladder 28 of a female patient's body. It will be understood that the depicted tissue stimulation electrodes may be coupled in common with a single conductor extending through the lead body to a single lead connector element adapted to be coupled to a unipolar tissue stimulation IPG to provide unipolar stimulation. Alternatively, the two conductors and lead connectors of a bipolar tissue stimulation lead may be each coupled to one or more tissue stimulation electrode to provide bipolar stimulation. The tissue stimulation electrodes apply the unipolar or bipolar stimulation to separate portions of the urethral tissue structure to ensure that the stimulation is applied to the most responsive contractile tissue to contract the urethra. In another variation, individual conductors and lead connectors adapted to be coupled to a multipolar tissue stimulation IPG may be coupled to each tissue stimulation electrode to apply stimulation in a time sequence to urethral tissue structure adjacent the tissue stimulation electrode. The tissue stimulation electrodes may take any suitable shape and be coupled to lead conductors in any convenient manner. The tissue stimulation leads depicted in FIGS. 26-29 exemplify some of these alternatives.

Figure 26:
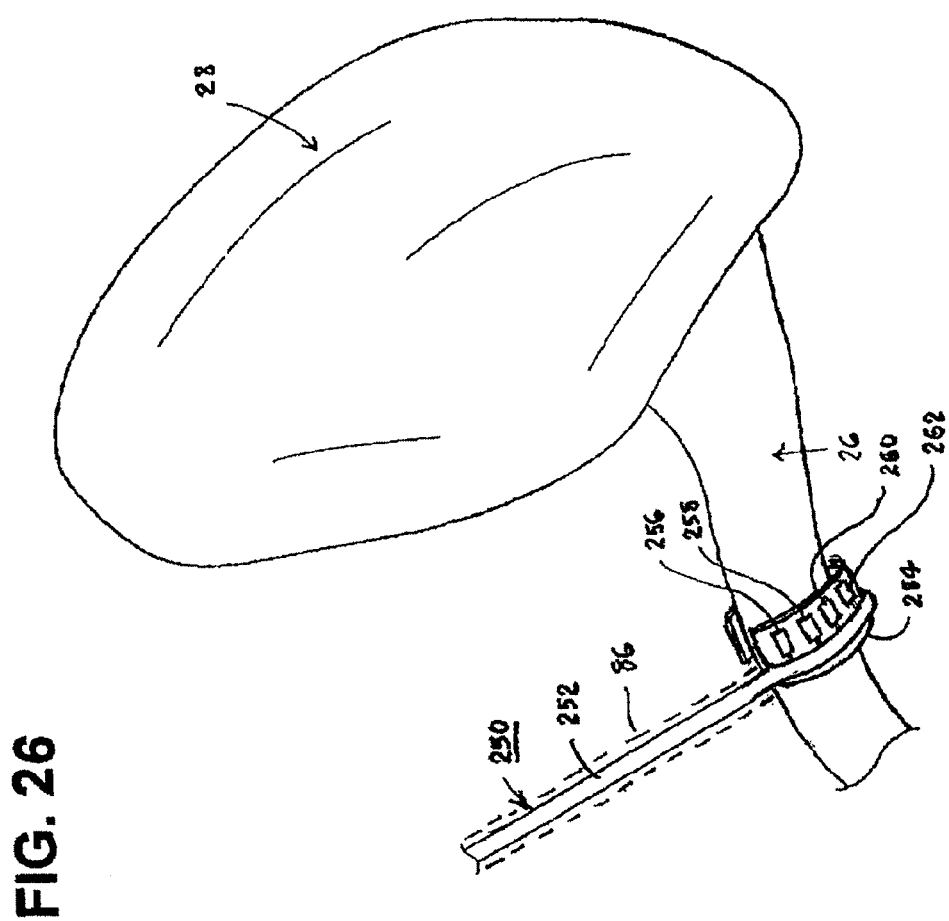
FIG. 26 is a schematic illustration of a distal segment of a tissue stimulation lead disposed in the tissue pathway to dispose a distal lead body band substantially surrounding the urethra and position a plurality of tissue stimulation electrodes supported by the band in selected stimulation sites in the urethral tissue structure.

In FIG. 26, the tissue stimulation lead 250 comprises a lead body 252 terminating in a resilient distal band 254 supporting a plurality of tissue stimulation electrodes 256, 258, 260, 262 etc., arrayed around the band 254 and coupled to respective lead conductors (not shown) extending from each electrode into the lead body 252. It will be understood that only two or more than the depicted four tissue stimulation electrodes (and respective lead conductors) may be disposed around the distal band 254 and extended through the lead body 252, respectively, to be coupled to a tissue stimulation IPG. The distal band 254 is not continuous, having an opening between a band free end and the end of the band affixed to the lead body 252. The distal band 254 may be formed of materials rendering the band resilient so that the opening may be expanded to manually place the band around the urethra 26 when it is inserted into the vaginal incision.

Figure 27:
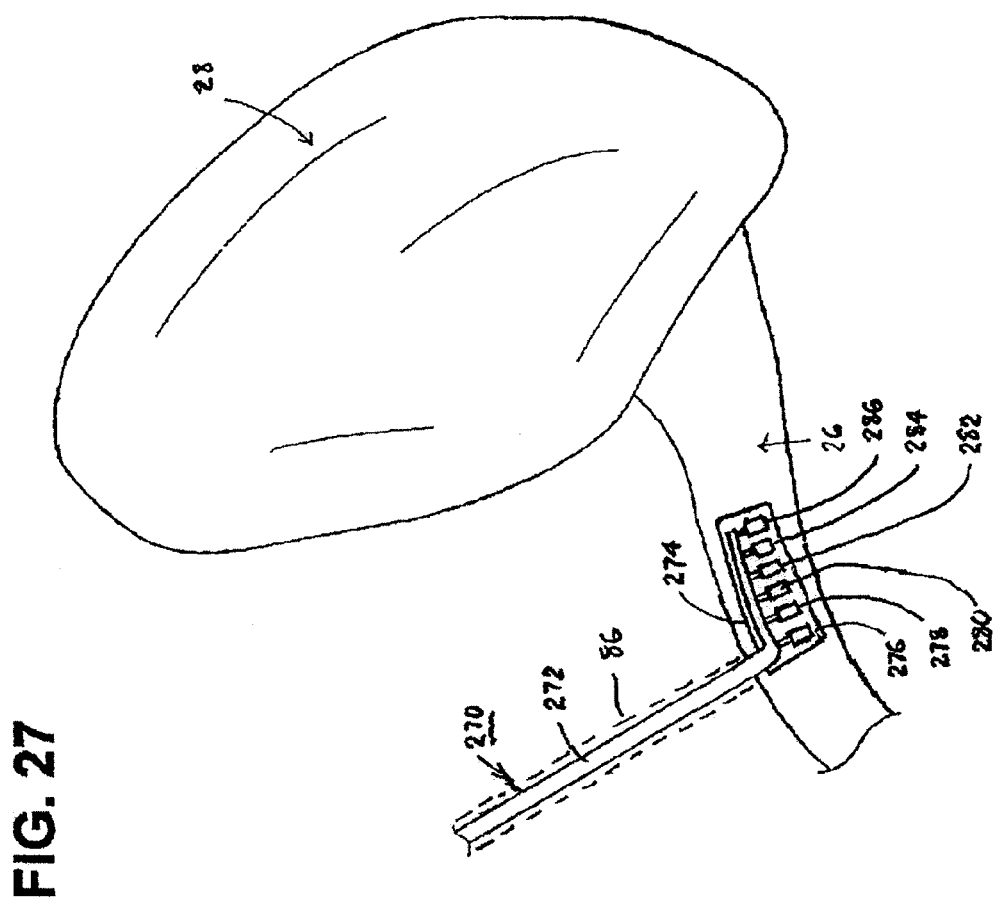
FIG. 27 is a schematic illustration of a distal segment of an L-shaped tissue stimulation lead disposed in the tissue pathway to dispose a distal body segment along the urethra and position a plurality of tissue stimulation electrodes supported by the distal body segment in selected stimulation sites in the urethral tissue structure.

In FIG. 27, an L-shaped tissue stimulation lead 270 comprises an L-shaped lead body 272 terminating in a distal body segment 274 supporting a plurality of tissue stimulation electrodes 276, 278, 280, 282, 284, 286, etc., arrayed along the segment 274 and coupled to respective lead conductors 288, 290, 292, 294, 296, 298, etc. It will be understood that fewer or more than the depicted six tissue stimulation electrodes and respective lead conductors may be disposed along the body segment 274 and extended through the lead body 272, respectively, to be coupled to a tissue stimulation IPG. The tissue stimulation electrodes 276, 278, 280, 282, 284, 286, etc., arrayed along the segment 274 may be ring-shaped extending around the distal body segment 274 or may be relatively planar disposed along a side of the distal body segment 274. The distal segment 274 may be manually placed extending along the urethra 26 when it is inserted into the vaginal incision.

Figure 28:
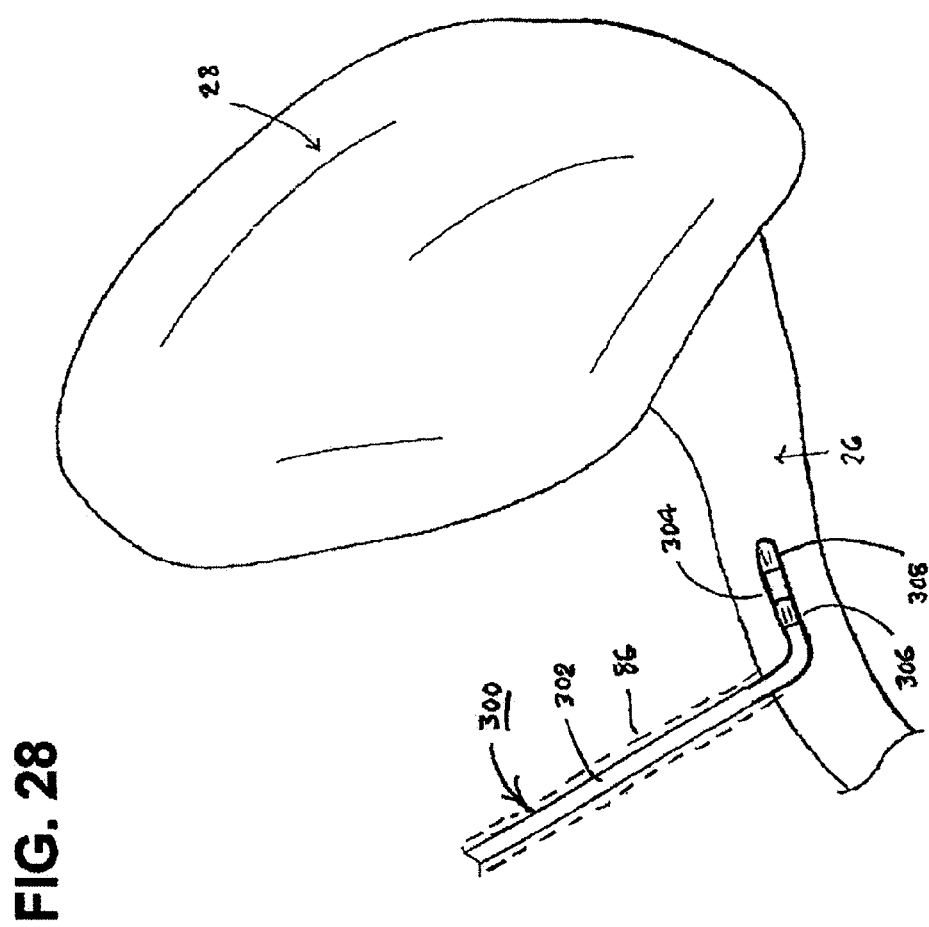
FIG. 28 is a schematic illustration of a distal segment of an L-shaped, unipolar or bipolar tissue stimulation lead disposed in the tissue pathway to dispose a distal body segment along the urethra and position a pair of tissue stimulation electrodes supported by the distal body segment in selected stimulation sites in the urethral tissue structure.

In FIG. 28, a simplified L-shaped unipolar or bipolar tissue stimulation lead 300 also comprises an L-shaped lead body 302 terminating in a distal body segment 304 supporting a pair of tissue stimulation electrodes 306 and 308. The ring-shaped, tissue stimulation electrodes 306 and 308 are spaced apart along the segment 304 and coupled to a single one or separate lead conductors (not shown) extending to a respective single one or pair of lead connector elements as described above. The distal body segment 304 may be manually placed extending along the urethra 26 when it is inserted into the vaginal incision.

It will be understood that the tissue stimulation electrodes 306 and 308 of the L-shaped tissue stimulation lead 300 may comprise a single, elongated electrode extending along the entire distal body segment 304. Moreover, it will be understood that any of the above-described fixation mechanisms may be incorporated into the L-shaped tissue stimulation lead 300.

Figure 29:
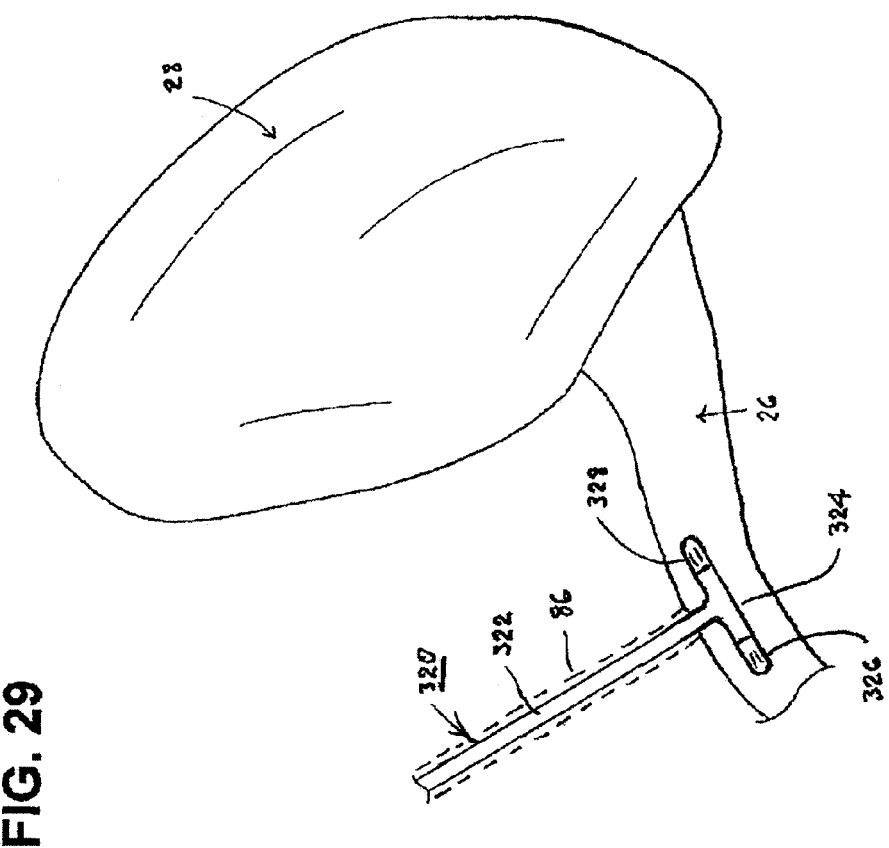
FIG. 29 is a schematic illustration of a distal segment of a T-shaped, unipolar or bipolar tissue stimulation lead disposed in the tissue pathway to dispose a distal body segment along the urethra and position a pair of tissue stimulation electrodes supported by the distal body segment in selected stimulation sites in the urethral tissue structure.

In FIG. 29, a simplified T-shaped unipolar or bipolar tissue stimulation lead 320 comprises a T-shaped lead body 322 terminating in a distal body segment 324 supporting a pair of tissue stimulation electrodes 326 and 328. The ring-shaped tissue stimulation electrodes 326 and 328 are spaced apart along the segment 324 and coupled to a single one or separate lead conductors (not shown) extending to a respective single one or pair of lead connector elements to be employed to provide unipolar or bipolar tissue stimulation of urethral tissue structure as described above. The distal body segment 324 may be manually placed extending along the urethra 26 when it is inserted into the vaginal incision.

It will be understood that the L-shaped tissue stimulation lead 270 depicted in FIG. 27 may be modified into a T-shape as depicted in FIG. 29 by coupling the lead body 272 to the distal body segment 274 intermediate tissue stimulation electrodes 280 and 282.

It will also be understood that the tissue stimulation electrodes 326 and 328 of the T-shaped tissue stimulation lead 320 may comprise a single, elongated electrode extending along the entire distal body segment 324. Moreover, it will be understood that any of the above-described fixation mechanisms may be incorporated into the T-shaped tissue stimulation lead 320.

Furthermore, it will also be understood that the L-shaped arrangement of the tissue stimulation electrodes 306 and 308 of the tissue stimulation lead 300 of FIG. 28 can be substituted for any of the distal electrodes disclosed in any of the embodiments of FIGS. 1-21. Similarly, it will be understood that the T-shaped arrangement of the tissue stimulation electrodes 326 and 328 of the tissue stimulation lead 320 of FIG. 29 can be substituted for any of the distal electrodes disclosed in any of the embodiments of FIGS. 1-21.

The lead bodies 252, 272, 302, 322 are extended through the tissue pathway 86 in any of the ways described above. A sheath or catheter may be employed as described herein in the passage of the lead bodies 252, 272, 302, 322 through the tissue pathway 86. A fixation mechanism of any of the above described types or others known in the art may be coupled to the lead bodies 252, 272, 302, 322.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical surgical procedures that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A stimulation lead assembly for placement in the pelvic floor and adapted to be coupled to an implantable pulse generator to deliver stimulation to selected stimulation sites comprising:
   a first stimulation lead comprising:
      a first elongated lead body extending between a first lead body proximal end and a first lead body distal end comprising a first insulating sheath and at least one electrical conductor within the first insulating sheath;
      a first proximal connector assembly having at least one lead connector element at the first lead body proximal end coupled to a proximal end of the electrical conductor;
      a first stimulation electrode at the first lead body distal end coupled to a distal end of the electrical conductor; and
      a first fixation mechanism extending along a portion of the lead body coupled to the first insulating sheath and extending laterally away from the lead body, the fixation mechanism formed of a material encouraging tissue ingrowth along the length of the portion of the lead body to stabilize the stimulation electrode at the stimulation site; and
   a second stimulation lead comprising:
      a second elongated lead body extending between a second lead body proximal end and a second lead body distal end comprising a second insulating sheath and at least one electrical conductor within the second insulating sheath;
      a second proximal connector assembly having at least one lead connector element at the second lead body proximal end coupled to a proximal end of the electrical conductor;
      a second stimulation electrode at the second lead body distal end coupled to a distal end of the electrical conductor; and
      a second fixation mechanism extending along a portion of the second lead body coupled to the second insulating sheath and extending laterally away from the second lead body, the second fixation mechanism formed of a material encouraging tissue ingrowth along the length of the portion of the second lead body to stabilize the stimulation electrode at the stimulation site; and
   an interconnecting portion coupled to the first and second lead body distal ends.

2. The stimulation lead assembly of claim 1, wherein the interconnecting portion comprises a segment of lead body extending between the first and second stimulation electrodes.

3. The stimulation lead assembly of claim 2, wherein the first and second fixation mechanisms are between the first and second stimulation electrodes.

4. The stimulation lead of claim 3, wherein the first and second fixation mechanisms comprises a sheet or tube of porous mesh having a mesh length and mesh width extending along the lead body.

5. The stimulation lead assembly of claim 1, wherein the interconnecting portion comprises an extension of the first and second fixation mechanisms between the first and second stimulation electrodes.

6. The stimulation lead of claim 5, wherein the first and second fixation mechanisms comprises a sheet or tube of porous mesh having a mesh length and mesh width respectively extending along the first and second elongated lead bodies.

7. The stimulation lead of claim 1, further comprising first and second protective sheath assemblies enclosing the respective first and second stimulation lead bodies and the at least portions of the first and second fixation mechanisms adapted to facilitate passage of the stimulation lead assembly through a tissue pathway.

8. The stimulation lead assembly of claim 1, wherein the first and second stimulation mechanisms each comprise a sheet of porous mesh, which is biased to maintain a substantially planar shape.

* * * * *